United States Patent
Duan

(10) Patent No.: US 10,906,901 B2
(45) Date of Patent: Feb. 2, 2021

(54) CRYSTAL FORM AND SALT FORM OF N-PHENYL-2-AMINOPYRIMIDINE COMPOUND, AND PREPARATION METHOD THEREFOR

(71) Applicant: HAINAN YUEKANG BIOMEDICINES CO., LTD., Hainan (CN)

(72) Inventor: Maosheng Duan, Hainan (CN)

(73) Assignee: HAINAN YUEKANG BIOMEDICINES CO., LTD., Haikou (CN)

( * ) Notice: Subject to any disclaimer, the term of this patent is extended or adjusted under 35 U.S.C. 154(b) by 0 days.

(21) Appl. No.: 16/631,276

(22) PCT Filed: Jun. 29, 2018

(86) PCT No.: PCT/CN2018/093607
§ 371 (c)(1),
(2) Date: Jan. 15, 2020

(87) PCT Pub. No.: WO2019/015463
PCT Pub. Date: Jan. 24, 2019

(65) Prior Publication Data
US 2020/0216444 A1 Jul. 9, 2020

(30) Foreign Application Priority Data
Jul. 19, 2017 (CN) .......................... 2017 1 0591403

(51) Int. Cl.
*C07D 471/04* (2006.01)
(52) U.S. Cl.
CPC ........ *C07D 471/04* (2013.01); *C07B 2200/13* (2013.01)

(58) Field of Classification Search
CPC .................................................... C07D 471/04
USPC ........................................................ 544/331
See application file for complete search history.

(56) References Cited

U.S. PATENT DOCUMENTS

2017/0355696 A1   12/2017   Jiang

FOREIGN PATENT DOCUMENTS

| CN | 106279160 | 1/1917 |
| CN | 106660993 | 5/1917 |
| CN | 104761585 | 7/2015 |
| CN | 105085489 | 11/2015 |
| WO | WO 2015/188777 | 12/2015 |

OTHER PUBLICATIONS

English translation of International Search Report issued in International Application No. PCT/CN2018/093607, dated Sep. 25, 2018.

*Primary Examiner* — Deepak R Rao
(74) *Attorney, Agent, or Firm* — Parker Highlander PLLC

(57) ABSTRACT

The present invention provides a new crystal form of a N-phenyl-2-aminopyrimidine compound, a crystal form of a pharmaceutically acceptable salt of said compound, and a preparation method for these crystal forms and use thereof. The present invention also relates to a pharmaceutical composition and a pharmaceutical preparation comprising the crystal form of said compound and the crystal form of the pharmaceutically acceptable salt of said compound, and use of these crystal forms, the pharmaceutical composition and the pharmaceutical preparation for treating diseases or conditions associated with the cell epidermal growth factor receptor (EGFR), for example, for treating or improving abnormal cell proliferative conditions, such as cancer.

6 Claims, 12 Drawing Sheets

CRYSTAL FORM AND SALT FORM OF N-PHENYL-2-AMINOPYRIMIDINE COMPOUND, AND PREPARATION METHOD THEREFOR

The present application is a national phase application under 35 U.S.C. § 371 of International Application No. PCT/CN2018/093607, filed Jun. 29, 2018, which claims priority to Chinese Patent Application No. 201710591403.1 entitled "CRYSTAL FORM AND SALT FORM OF N-PHENYL-2-AMINOPYRIMIDINE COMPOUND, AND PREPARATION METHOD THEREOF" filed with State Intellectual Property Office on Jul. 19, 2017, and the entire contents of each of which are incorporated herein by reference.

FIELD

The present disclosure belongs to the field of medical technology, and relates to the crystal form and salt form of N-phenyl-2-aminopyrimidine compound having an inhibitory effect on epidermal growth factor receptor (EGFR) and useful to treat or ameliorate an abnormal cell proliferative condition (such as cancer), and preparation method thereof. Specifically, the present disclosure relates to the crystal form of N-(2-methoxy-4-($N^1,N^2,N^2$-trimethyl-1,2-ethylenediamine-1-yl)-5-acrylamidephenyl)-4-(8-m ethylimidazo[1,2-a]pyridin-3-yl)pyrimidin-2-amine and salt thereof, and method for producing the same.

BACKGROUND

Cancer is one of the leading causes of death, second only to cardiovascular disease. According to data released by the World Health Organization, there were 14 million new cancer patients and 8.2 million cancer-related deaths worldwide in 2012. Statistics from research in the Cancer Hospital of the Chinese Academy of Medical Sciences and the National Cancer Center in 2016 showed that in China, there were 4.292 million new cancer patients and 2.814 million cancer-related deaths in 2015. As lifestyle changes, population aging, and environmental changes, the incidence and mortality of cancer rise quickly. It is estimated that in the next two decades, the annual number of new cancer cases worldwide will increase by 70% to about 25 million. Therefore, the prevention and treatment of cancer face severe challenges.

According to statistics, the top three cancers worldwide in terms of incidence are lung cancer, prostate cancer and rectal cancer in male, and breast cancer, colon cancer and lung cancer in female. Considering male and female together, lung cancer has the highest incidence and the highest mortality rate. Clinically, non-small cell lung cancer (NSCLC) approximately accounts for 85% of the total lung cancer cases. Due to the lack of obvious symptoms in the early stage, most patients are already in the middle and late stages at the time of consultation, and thus losing a good opportunity for treatment. According to statistics from the American Cancer Society, in the approximately 200,000 new NSCLC patients annually, approximately more than 65% have advanced to stage III or IV at the time of diagnosis. Except for some stage III NSCLC which can be surgically resected by induction therapy, most patients only can be treated with chemotherapy. However, chemotherapeutic drugs have significant toxicity and side effect, causing great pain to the patients. Therefore, there is urgent need for the majority of patients, especially the patients in the advanced stage to find efficient drugs for targeted treatment of various cancers.

Epidermal growth factor receptor (EGFR) is a member of the transmembrane protein tyrosine kinases which belong to erbB receptor family. The binding between EGFR and EGF (epidermal growth factor) results in homodimerization of the receptors, or heterodimerization between the receptor and member of another family, such as erbB2 (HER2), erbB3 (HER3), or erbB4 (HER4). The homodimerization and/or heterodimerization of erbB receptors lead to the phosphorylation of key tyrosine in the intracellular domain, which in turn regulates many intracellular signaling pathways involved in cell proliferation and survival. Abnormal regulation of erbB signaling in the body may promote cell diffusion, invasion, metastasis, angiogenesis, and tumor formation. The mechanism of this type of tyrosine kinase signaling transduction has been described in many human cancers, including cancers in lung, head and neck, and chest. Therefore, the erbB receptor family is a potential target for anticancer drugs. Some EGFR-targeted drugs have been marketed, including Gifitinib (IRESSA™), Erlotinib (TARCEVA™), Lapatinib (TYKERB™), Icotinib (Conmana) and so on. The signaling of erbB receptor and its involvement in tumorigenesis are discussed in detail in the literatures (New England Journal of Medicine, 2008, Vol. 358, 1160-74; Biochemical and Biophysical Research Communications, 2004, Vol. 319, 1-11).

In 2004, the response of non-small cell lung cancer (NSCLC) with epidermal growth factor receptor activating mutations to the treatment of gefitinib was reported (Science, 2004, Vol. 304, 1497-500 and New England Journal of Medicine (2004) Vol. 350, 2129-39). The most common epidermal growth factor receptor activating mutations (L858R and delE746-A750) show increasing affinity to tyrosine kinase inhibitors (such as gefitinib and erlotinib) and decreasing affinity to ATP when compared to the wild-type (WT) receptor, so that the aforementioned small molecule tyrosine kinase inhibitors (such as gefitinib and erlotinib) can effectively inhibit the growth of lung cancer cells. However, on the other hand, long-term use of small molecule tyrosine kinase inhibitors (such as gefitinib and erlotinib) has led to gefitinib and erlotinib resistance in some patients. Studies have shown that, for example, the mutation of gatekeeper residue T790M has been detected in 50% of patients with drug resistance in clinic. This mutation not only reduces the binding of gefitinib or erlotinib to EGFR, but also changes the affinity to ATP back to the same level as the wild-type (WT) epidermal growth factor receptor.

This mutation causes serious consequence of drug resistance in the existing therapies targeting EGFR, that is, no suitable drugs can be used for those patients again. Therefore, there is a urgent need to develop a novel EGFR inhibitor which can avoid T\M mutation in the gatekeeper gene for treating related cancers.

It is necessary for the novel inhibitors to exhibit selectivity to wild-type EGFR compared with the activating mutant forms of EGFR (such as L858R, delE746-A750 or exon 19 deletion (Ex19del)) and/or drug-resistant mutant forms of EGFR (such as T790M EGFR mutant), because the inhibition to wild-type EGFR will bring toxicity and side effects. In order to further overcome the drug resistance caused by the T790M mutation, a novel class of irreversible ATP competitive inhibitors (such as PF00299804, CI-1033, HKI-272, AZD9291, and the like) has entered clinical research stage or has been approved for marketing. These irreversible inhibitors contain a Michael addition acceptor, which can be covalently coupled to the thiol (—SH) of a conserved amino acid (Cys797) at the binding site of the receptor. This irreversible covalent bond between the inhibitor and EGFR usually stronger than the bond between reversible inhibitor and EGFR (Journal of Medicinal Chemistry, 2009, 52, 1231-1236). Such inhibitors exhibit high activity and strong selectivity.

Nevertheless, the clinical trial results of the irreversible inhibitors listed above indicate that these inhibitors still have certain limitations, such as side effects due to off-target effects or low selectivity, and poor pharmacokinetic properties, as well as unknown pharmacological and toxicological characterization of metabolites in the body. Therefore, the development of new, efficient and safe irreversible EGFR inhibitors has great clinical significance and application prospects.

N-(2-methoxy-4-($N^1,N^2,N^2$-trimethyl-1,2-ethylenediamine-1-yl)-5-acrylamidephenyl)-4-(8-methylimidazo[1,2-a]pyridin-3-yl)pyrimidin-2-amine (hereinafter referred to as "Compound 1") is a novel EGFR inhibitor represented by Formula (I):

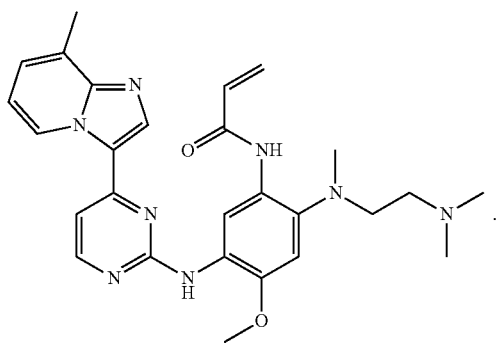

Formula (I)

The above compound is described in Chinese Patent Application 201610679161.7, and the content of which can be used as a reference for the present application. In the enzymatic activity test and Celltiter-Glo cell proliferation test, Compound 1 showed significant inhibitory activity against EGFR and strong inhibitory activity on cells with single or double EGFR mutations. In addition, the compound showed high selectivity to EGFR mutants. However, the inventors of the present invention found that Compound 1 was still unsatisfied in terms of stability, solubility, and bioavailability in drug research.

SUMMARY

In order to solve the problems of stability, solubility, bioavailability and the like of the above compound N-(2-methoxy-4-($N^1,N^2,N^2$-trimethyl-1,2-ethylenediamine-1-yl)-5-acrylamidephenyl)-4-(8-m ethylimidazo[1,2-a]pyridin-3-yl)pyrimidin-2-amine (Compound 1), the present disclosure provides a crystal form A of Compound 1 and salts thereof, and method for producing the same.

The first aspect of the present disclosure is to provide a crystal form A of Compound 1, having diffraction peaks in X-ray powder diffraction (XRPD) at diffraction angles (2θ±0.2°) of 6.625, 10.289, 13.791, 15.235, 16.019, 16.353, 17.087, 19.510, 19.992, 21.194, 21.992, 22.724, 24.338, 24.997, 25.876 and 27.245, as shown in Table 1 below.

TABLE 1

| Number | Angle 2-θ | Interplanar Spacing Angstrom | Peak Intensity Intensity Counts | Relative Intensity % |
|---|---|---|---|---|
| 1 | 6.625 | 13.331 | 54597.000 | 100.000 |
| 2 | 10.289 | 8.591 | 1691.000 | 3.100 |
| 3 | 13.791 | 6.416 | 2471.000 | 4.500 |
| 4 | 15.235 | 5.811 | 1362.000 | 2.500 |
| 5 | 16.019 | 5.528 | 2124.000 | 3.900 |
| 6 | 16.353 | 5.416 | 1569.000 | 2.900 |
| 7 | 17.087 | 5.185 | 848.000 | 1.600 |
| 8 | 19.510 | 4.546 | 2218.000 | 4.100 |
| 9 | 19.992 | 4.438 | 1268.000 | 2.300 |
| 10 | 21.194 | 4.189 | 1169.000 | 2.100 |
| 11 | 21.992 | 4.038 | 1083.000 | 2.000 |
| 12 | 22.724 | 3.910 | 848.000 | 1.600 |
| 13 | 24.338 | 3.654 | 1724.000 | 3.200 |
| 14 | 24.997 | 3.559 | 1184.000 | 2.200 |
| 15 | 25.876 | 3.440 | 905.000 | 1.700 |
| 16 | 27.245 | 3.271 | 1837.000 | 3.400 |

The X-ray powder diffraction of the crystal form A of Compound 1 according to the present disclosure is substantially as shown in FIG. 1.

The DSC (FIG. 2) of the crystal form A of Compound 1 according to the present disclosure indicates that the maximum endothermic transition of the crystal form is at about 174.15° C.

The TGA (FIG. 2) of the crystal form A of Compound 1 according to the present disclosure shows only a small amount of weight loss when heating from 50° C. to 225° C.

The Dynamic Vapor Sorption (DVS) curve at 25° C. (FIG. 3) of the crystal form A of Compound 1 according to the present disclosure shows that the crystal form A has almost no hygroscopicity.

The results of the accelerated stability test of the crystal form A of Compound 1 according to the present disclosure show that the crystal form A has good chemical stability when avoiding the light, and the crystal structure of the sample does not change after the accelerated stability test. TGA result shows that the crystal form A sample absorbs little water. These properties provide support for the development and application of Compound 1 as a drug.

The second aspect of the present disclosure is to provide a method of producing the crystal form A of Compound 1. The preparation method comprises the following steps: suspending Compound 1 in a mixed solvent of acetonitrile and water, heating and dissolving with stirring; cooling the resulting solution overnight with stirring until room temperature, performing precipitation, filtration, and collecting solids; and subjecting the resulting solids to vacuum drying to obtain the crystal powder of Compound 1, which is the crystal form A of Compound 1.

The third aspect of the present disclosure is to provides a crystal form of a pharmaceutically acceptable salt of Compound 1, wherein the pharmaceutically acceptable salt is a conventional inorganic or organic salt in the art, wherein the inorganic salt is preferably hydrochloride, hydrobromide, phosphate, sulfate or perchlorate, and the organic salt is preferably acetate, oxalate, maleate, tartrate, succinate, citrate, succinate or malonate. Other pharmaceutically acceptable salts include adipate, sodium alginate, ascorbate, aspartate, besylate, benzoate, bisulfate, borate, butyrate, camphorate, camphor sulfonate, citrate, cyclopentane propionate, digluconate, dodecyl sulfate, ethanesulfonate, formate, fumarate, gluceptate, glycerolphosphate, gluconate, hernisulfate, heptylate, hexanoate, hydriodate, 2-hydroxyethanesulfonate, lactobionate, lactate, laurate, lauryl sulfate, malate, maleate, malonate, mesylate, 2-naphthalenesulfonate, nicotinate, nitrate, oleate, oxalate, palmitate, pamoate, pectate, persulfate, 3-phenpropionate, phosphate, picrate, pivalate, propionate, stearate, succinate, sulfate, tartrate, thiocyanate, tosilate, undecanoate, valerate, and the like. More preferably, the pharmaceutically acceptable salt is hydrochloride, mesylate, fumarate, benzoate, maleate, L-tartrate and succinate, which have advantages over other salts in stability, character and bioavailability.

The fourth aspect of the present disclosure is to provide a method of producing a crystal form of a pharmaceutically acceptable salt of Compound 1, wherein the crystal form of the pharmaceutically acceptable salt of Compound 1 can be prepared according to a conventional salt-forming method in the art.

In a preferred embodiment of the present disclosure, the method of producing a crystal form of a pharmaceutically acceptable salt of Compound 1 comprises the following steps: adding a solution of Compound 1 in methanol to a corresponding organic solvent, wherein for example, the organic solvent is one or more selected from acetonitrile, acetone, ethyl acetate and isopropyl alcohol; heating the resulting solution until clear; adding the corresponding acid in equivalent amounts with stirring, and solids are generated after a while; and stirring the resulting suspension for half an hour, collecting the solids by filtration, and subjecting the solids to vacuum drying to obtain the crystal of the corresponding salt.

The fifth aspect of the present disclosure is to provide a crystal form I of the hydrochloride of Compound 1, having diffraction peaks in X-ray powder diffraction at diffraction angles (2θ±0.2°) of 3.600, 7.262, 10.018, 10.981, 11.311, 18.381, 22.096, 25.879, 27.110 and 29.629, as shown in Table 2 below.

TABLE 2

| Number | Angle 2-θ | Interplanar Spacing Angstrom | Peak Intensity Intensity Counts | Relative Intensity % |
|---|---|---|---|---|
| 1 | 3.600 | 24.526 | 5756.000 | 100.000 |
| 2 | 7.262 | 12.163 | 516.000 | 9.000 |
| 3 | 10.018 | 8.823 | 452.000 | 7.900 |
| 4 | 10.981 | 8.051 | 616.000 | 10.700 |
| 5 | 11.311 | 7.816 | 380.000 | 6.600 |
| 6 | 18.381 | 4.823 | 310.000 | 5.400 |
| 7 | 22.096 | 4.020 | 1103.000 | 19.200 |
| 8 | 25.879 | 3.440 | 1308.000 | 22.700 |
| 9 | 27.110 | 3.287 | 227.000 | 3.900 |
| 10 | 29.629 | 3.013 | 606.000 | 10.500 |

The sixth aspect of the present disclosure is to provide a crystal form II of the mesylate of Compound 1, having diffraction peaks in X-ray powder diffraction at diffraction angles (2θ±0.2°) of 4.015, 9.963, 11.032, 12.099, 16.179, 18.353, 19.762, 20.250, 21.565, 22.541, 24.507, 29.554 and 33.666, as shown in Table 3 below.

TABLE 3

| Number | Angle 2-θ | Interplanar Spacing Angstrom | Peak Intensity Intensity Counts | Relative Intensity % |
|---|---|---|---|---|
| 1 | 4.015 | 21.987 | 3734.000 | 100.000 |
| 2 | 9.963 | 8.871 | 492.000 | 13.200 |
| 3 | 11.032 | 8.014 | 329.000 | 8.800 |
| 4 | 12.099 | 7.309 | 631.000 | 16.900 |
| 5 | 16.179 | 5.474 | 2208.000 | 59.100 |
| 6 | 18.353 | 4.830 | 947.000 | 25.400 |
| 7 | 19.762 | 4.489 | 1021.000 | 27.300 |
| 8 | 20.250 | 4.382 | 680.000 | 18.200 |
| 9 | 21.565 | 4.117 | 492.000 | 13.200 |
| 10 | 22.541 | 3.941 | 256.000 | 6.900 |
| 11 | 24.507 | 3.629 | 244.000 | 6.500 |
| 12 | 29.554 | 3.020 | 243.000 | 6.500 |
| 13 | 33.666 | 2.660 | 216.000 | 5.800 |

The seventh aspect of the present disclosure is to provide a crystal form III of the fumarate of Compound 1, having diffraction peaks in X-ray powder diffraction at diffraction angles (2θ±0.2°) of 6.254, 6.949, 9.794, 11.598, 13.560, 14.837, 16.094, 18.967, 19.675, 20.855, 22.343, 23.728 and 25.950, as shown in Table 4 below.

TABLE 4

| Number | Angle 2-θ | Interplanar Spacing Angstrom | Peak Intensity Intensity Counts | Relative Intensity % |
|---|---|---|---|---|
| 1 | 6.254 | 14.122 | 9568.000 | 100.000 |
| 2 | 6.949 | 12.711 | 1138.000 | 11.900 |
| 3 | 9.794 | 9.024 | 993.000 | 10.400 |
| 4 | 11.598 | 7.624 | 834.000 | 8.700 |
| 5 | 13.560 | 6.525 | 1132.000 | 11.800 |
| 6 | 14.837 | 5.966 | 1586.000 | 16.600 |
| 7 | 16.094 | 5.503 | 2123.000 | 22.200 |
| 8 | 18.967 | 4.675 | 807.000 | 8.400 |
| 9 | 19.675 | 4.509 | 656.000 | 6.900 |
| 10 | 20.855 | 4.256 | 963.000 | 10.100 |
| 11 | 22.343 | 3.976 | 930.000 | 9.700 |
| 12 | 23.728 | 3.747 | 931.000 | 9.700 |
| 13 | 25.950 | 3.431 | 884.000 | 9.200 |

The eighth aspect of the present disclosure is to provide a crystal form IV of the benzoate of Compound 1, of which the X-ray powder diffraction data are shown in Table 5 below.

TABLE 5

| Number | Angle 2-θ° | d Angstrom | Intensity Counts | Relative Intensity % | Net Area Cps × 2-θ° | Relative Area (%) | Width at Half Maximum 2-θ° |
|---|---|---|---|---|---|---|---|
| 1 | 7.994 | 11.05128 | 689 | 28.2 | 3.53 | 19.76 | 0.158 |
| 2 | 8.696 | 10.16079 | 1475 | 60.4 | 6.001 | 33.60 | 0.099 |
| 3 | 10.307 | 8.57577 | 2441 | 100 | 17.86 | 100.00 | 0.214 |
| 4 | 14.471 | 6.11597 | 581 | 23.8 | 4.981 | 27.89 | 0.216 |
| 5 | 16.638 | 5.32353 | 939 | 36.5 | 5.452 | 30.53 | 0.18 |
| 6 | 17.377 | 5.09926 | 954 | 39.1 | 5.167 | 28.93 | 0.15 |

TABLE 5-continued

| Number | Angle 2-θ° | d Angstrom | Intensity Counts | Relative Intensity % | Net Area Cps × 2-θ° | Relative Area (%) | Width at Half Maximum 2-θ° |
|---|---|---|---|---|---|---|---|
| 7 | 17.967 | 4.93319 | 466 | 19.1 | 1.583 | 8.86 | 0.157 |
| 8 | 19.723 | 4.49775 | 345 | 14.1 | 1.813 | 10.15 | 0.181 |
| 9 | 20.529 | 4.32294 | 993 | 40.7 | 8.02 | 44.90 | 0.192 |
| 10 | 22.933 | 3.87491 | 750 | 30.7 | 3.376 | 18.90 | 0.17 |
| 11 | 23.383 | 3.80126 | 683 | 26 | 4.268 | 23.90 | 0.319 |

The ninth aspect of the present disclosure is to provide a crystal form V of the maleate of Compound 1, of which the X-ray powder diffraction data are shown in Table 6 below.

TABLE 6

| Number | Angle 2-θ | Interplanar Spacing Angstrom | Peak Intensity Intensity Counts | Relative Intensity % |
|---|---|---|---|---|
| 1 | 5.435 | 16.248 | 989.000 | 16.800 |
| 2 | 7.966 | 11.090 | 2057.000 | 34.900 |
| 3 | 8.574 | 10.304 | 3481.000 | 59.000 |
| 4 | 10.304 | 8.578 | 5896.000 | 100.000 |
| 5 | 12.990 | 6.810 | 805.000 | 13.700 |
| 6 | 13.587 | 6.512 | 937.000 | 15.900 |
| 7 | 13.817 | 6.404 | 1271.000 | 21.600 |
| 8 | 14.383 | 6.153 | 1023.000 | 17.400 |
| 9 | 14.806 | 5.978 | 1256.000 | 21.300 |
| 10 | 15.947 | 5.553 | 946.000 | 16.000 |
| 11 | 16.654 | 5.319 | 1853.000 | 31.400 |
| 12 | 17.236 | 5.141 | 1219.000 | 20.700 |
| 13 | 17.914 | 4.948 | 2284.000 | 38.700 |
| 14 | 19.024 | 4.661 | 877.000 | 14.900 |
| 15 | 19.922 | 4.453 | 1310.000 | 22.200 |
| 16 | 20.700 | 4.287 | 1625.000 | 27.600 |
| 17 | 23.252 | 3.822 | 4230.000 | 71.700 |
| 18 | 26.113 | 3.410 | 1208.000 | 20.500 |
| 19 | 27.052 | 3.293 | 2433.000 | 41.300 |

The tenth aspect of the present disclosure is to provide a crystal form VI of the L-tartrate of Compound 1, of which the X-ray powder diffraction data are shown in Table 7 below.

TABLE 7

| Number | Angle 2-θ | Interplanar Spacing Angstrom | Peak Intensity Intensity Counts | Relative Intensity % |
|---|---|---|---|---|
| 1 | 8.576 | 10.302 | 5902.000 | 100.000 |
| 2 | 13.386 | 6.609 | 297.000 | 5.000 |
| 3 | 14.330 | 6.176 | 364.000 | 6.200 |
| 4 | 14.768 | 5.994 | 498.000 | 8.400 |
| 5 | 16.702 | 5.304 | 461.000 | 7.800 |
| 6 | 17.256 | 5.135 | 747.000 | 12.700 |
| 7 | 17.652 | 5.020 | 377.000 | 6.400 |
| 8 | 19.104 | 4.642 | 246.000 | 4.200 |
| 9 | 20.004 | 4.435 | 473.000 | 8.000 |
| 10 | 20.610 | 4.306 | 451.000 | 7.600 |
| 11 | 21.245 | 4.179 | 978.000 | 16.600 |
| 12 | 22.437 | 3.959 | 387.000 | 6.600 |
| 13 | 22.813 | 3.895 | 312.000 | 5.300 |
| 14 | 23.722 | 3.748 | 225.000 | 3.800 |
| 15 | 28.309 | 3.150 | 237.000 | 4.000 |

The eleventh aspect of the present disclosure is to provide a crystal form VII of the succinate of Compound 1, of which the X-ray powder diffraction data are shown in Table 8 below.

TABLE 8

| Number | Angle 2-θ | Interplanar Spacing Angstrom | Peak Intensity Intensity Counts | Relative Intensity % |
|---|---|---|---|---|
| 1 | 6.905 | 12.792 | 1192.000 | 46.200 |
| 2 | 9.328 | 9.473 | 1855.000 | 71.800 |
| 3 | 9.786 | 9.031 | 1874.000 | 72.600 |
| 4 | 12.084 | 7.318 | 882.000 | 34.200 |
| 5 | 12.732 | 6.947 | 612.000 | 23.700 |
| 6 | 14.684 | 6.028 | 688.000 | 26.600 |
| 7 | 15.610 | 5.672 | 545.000 | 21.100 |
| 8 | 16.675 | 5.312 | 1196.000 | 46.300 |
| 9 | 17.670 | 5.015 | 471.000 | 18.200 |
| 10 | 20.083 | 4.418 | 892.000 | 34.500 |
| 11 | 20.761 | 4.275 | 1292.000 | 50.000 |
| 12 | 22.111 | 4.017 | 2248.000 | 87.100 |
| 13 | 23.545 | 3.775 | 534.000 | 20.700 |
| 14 | 24.560 | 3.622 | 2582.000 | 100.000 |
| 15 | 25.950 | 3.431 | 805.000 | 31.200 |
| 16 | 28.191 | 3.163 | 578.000 | 22.400 |
| 17 | 29.647 | 3.011 | 636.000 | 24.600 |

The twelfth aspect of the present disclosure is to provide a pharmaceutical composition comprising a therapeutically effective amount of the above crystal form A of Compound 1 or the above crystal forms of the pharmaceutically acceptable salts of Compound 1, wherein the pharmaceutical composition may further comprise one or more pharmaceutically acceptable carriers.

A thirteenth aspect of the present disclosure is to provide use of the above crystal form A of Compound 1 or the above crystal forms of the pharmaceutically acceptable salts of Compound 1 in the manufacture of a medicament for the prevention or treatment of diseases or conditions associated with epidermal growth factor receptor, wherein the diseases or conditions are cancers, preferably non-small cell lung cancer.

The crystal form A of Compound 1 or the above crystal forms of the pharmaceutically acceptable salts of Compound 1 according to the present disclosure has excellent properties in terms of solubility, stability and the like, and can be used for effectively preventing or treating diseases or conditions associated with epidermal growth factor receptor, which may be, for example, cancers, such as non-small cell lung cancer.

DETAILED DESCRIPTION

Figure 1:
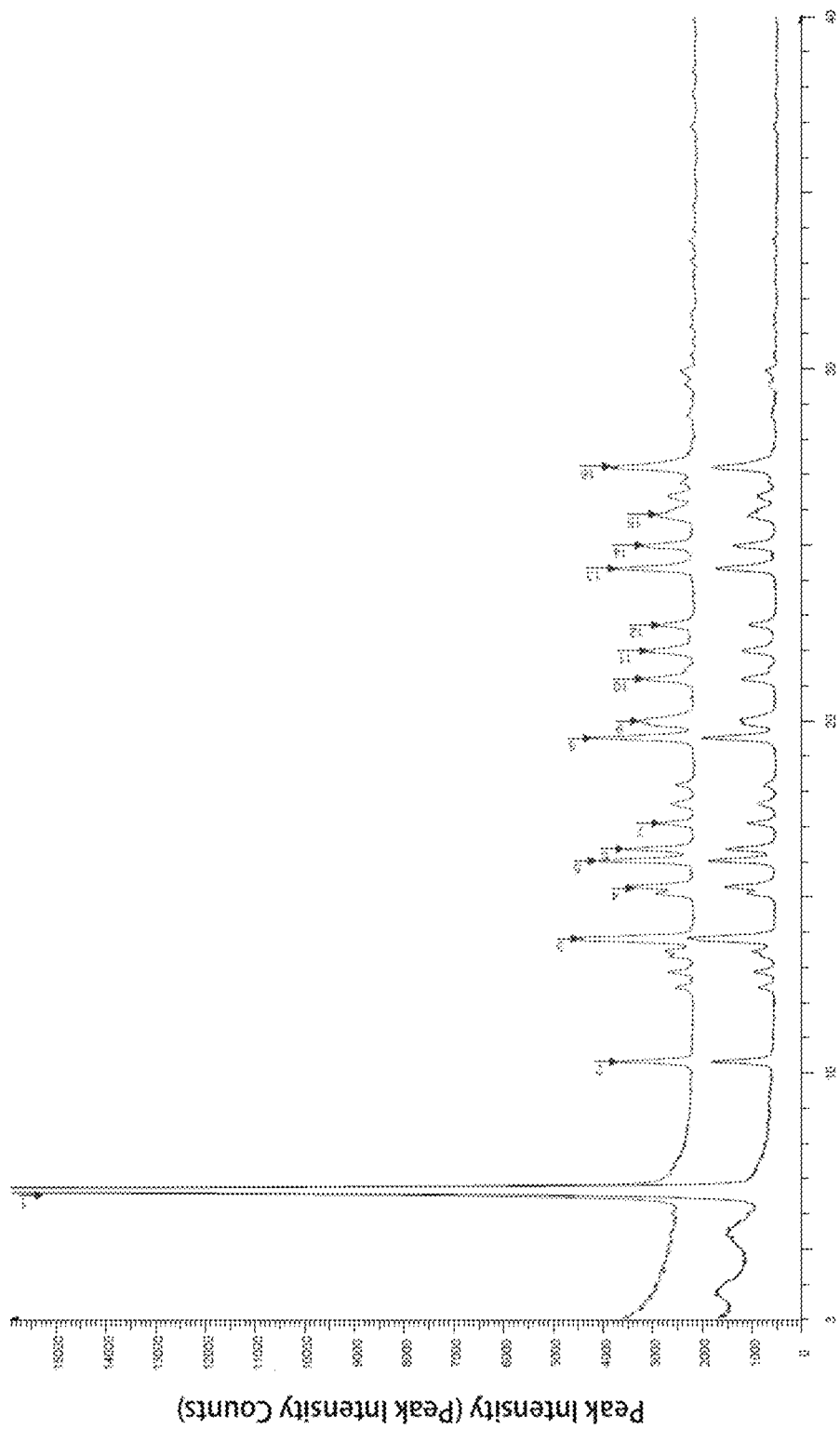
FIG. 1: XRPD pattern of the crystal form A of Compound 1.

The compounds of the invention and the preparation methods can also be further understood by the examples, which illustrate some methods for preparing or using the compounds. It should be understood that these examples would not limit the scope of the present invention. Changes based on the art or further developments according to the present disclosure are considered to fall within the scope of the invention described herein and claimed below.

The pharmaceutically acceptable salt of the present disclosure is a salt formed via acid-base reaction, wherein the salt is a salt of N-(2-methoxy-4-($N^1,N^2,N^2$-trimethyl-1,2-ethylenediamine-1-yl)-5-acrylamidephenyl)-4-(8-methyl-imidazo[1,2-a]pyridin-3-yl)pyrimidin-2-amine (Compound 1), and wherein the acid is selected from the group consisting of hydrochloric acid, methylsulfonic acid, fumaric acid, benzoic acid, maleic acid, L-tartaric acid and succinic acid.

I. Synthesis Method of Compound 1

Synthesis Pathway

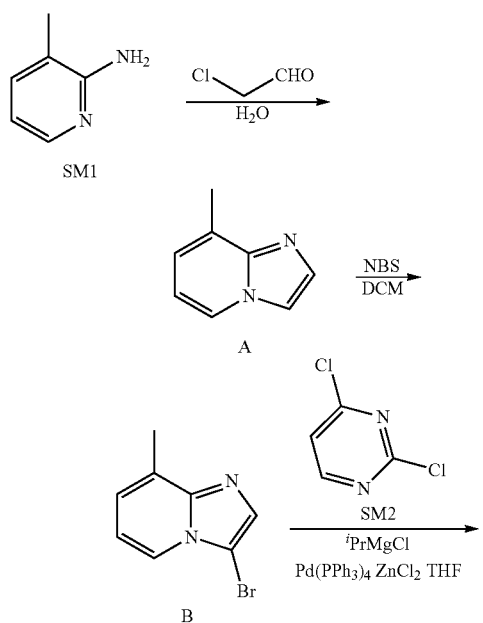

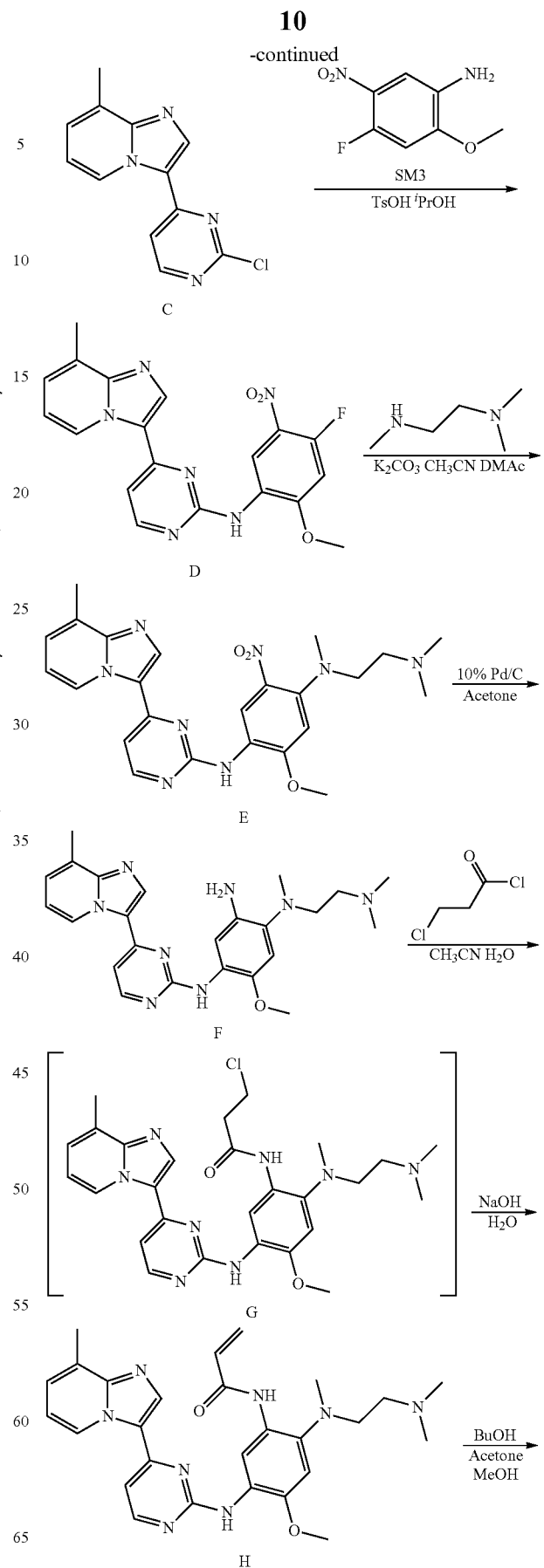

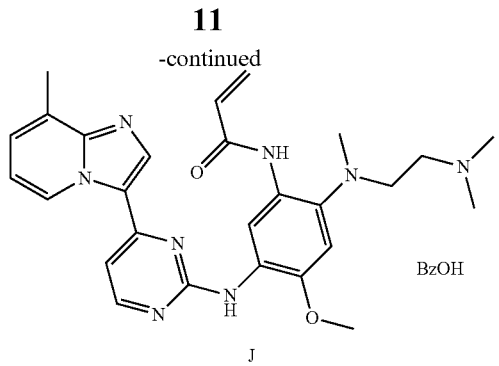

J

Synthesis Steps
Step 1: Preparation of Intermediate A

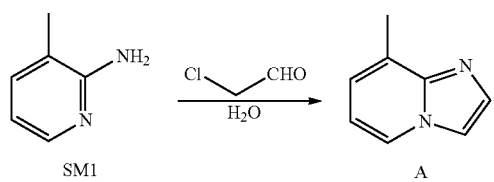

SM1 (7.0 kg, 1.0 eq) and purified water (21.0 kg, 3.0×) were added to a 30 L glass reaction kettle, and dissolved by stirring. 40% chloroacetaldehyde (15.3 kg, 1.2 eq) was added. The temperature was raised to 60-65° C., and the reaction was carried out at this temperature for 3 h. The completion of the reaction was detected.

The reaction solution was slowly cooled to room temperature, and NaOH aqueous solution (20 wt %, 14.35 kg, 1.1 eq) prepared in advance was added to neutralize the reaction. The resulting solution was extracted 3 times with dichloromethane (28.0 kg/4.0×, 28.0 kg/4.0×, 18.0 kg/2.66×). The organic phases were combined, washed with purified water (21.0 kg, 3.0×) and 10% sodium chloride solution (21.0 kg, 3.0×) once respectively, dried over anhydrous magnesium sulfate (2.8 kg, 0.4×) and filtered to give the dichloromethane solution of intermediate A with a purity of 99.0%, which was directly used for the preparation of intermediate B.

Step 2: Preparation of Intermediate B

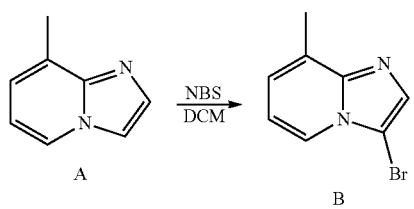

The dichloromethane solution of intermediate A in the previous step was completely added to a 30 L glass reaction kettle. N-bromosuccinimide (11.5 kg, 1.0 eq) was added in batches while controlling the temperature at 20~25° C., and the reaction was carried out at this temperature for 3 hours. The completion of the reaction was detected.

5% sodium bisulfite aqueous solution (16.9 kg, 0.1 eq) was slowly added dropwise to the reaction solution at 20~25° C. to quench the reaction, and after the addition, the resulting solution was stirred at 20~25° C. for 0.5 hour. After standing, the layers showed up. The aqueous phase was extracted once with dichloromethane (17.0 kg, 2.66×). The organic phases were combined, washed with purified water (21.0 kg, 3.0×) and 10% sodium chloride aqueous solution (21.0 kg, 3.2×) once respectively, dried over anhydrous magnesium sulfate (2.5 kg, 0.36×) and filtered. The filtrate was concentrated under reduced pressure at 40~45° C. until no solvent came out. Ethanol (11.0 kg, 2.0 V) was added to the concentrate to continue concentrate until no solvent came out. Ethanol (11.0 kg, 1.8×) was added, the temperature was raised to 40~45° C., and purified water (35.0 kg, 5.0V) was slowly added dropwise. After the addition, the temperature was slowly lowered to 0~5° C. and held for 1 h with stirring. A large amount of solid was precipitated and then filtered. The filter cake was washed with purified water (14.0 kg, 2.0×) and dried to give 11.76 kg of intermediate B with a purity of 99.85% and a moisture content of 3.72%. Yield: 91%.

LC-MS m/z (ES$^+$): (M+H$^+$) 211.3 (100%), 213.3 (97.7%),
$^1$HNMR (400 MHz, d$_6$-DMSO) δ 8.12 (m, 1H), 7.63 (s, 1H), 7.13 (m, 1H), 6.95 (s, 1H), 2.46 (s, 3H).

Step 3: Preparation of Intermediate C

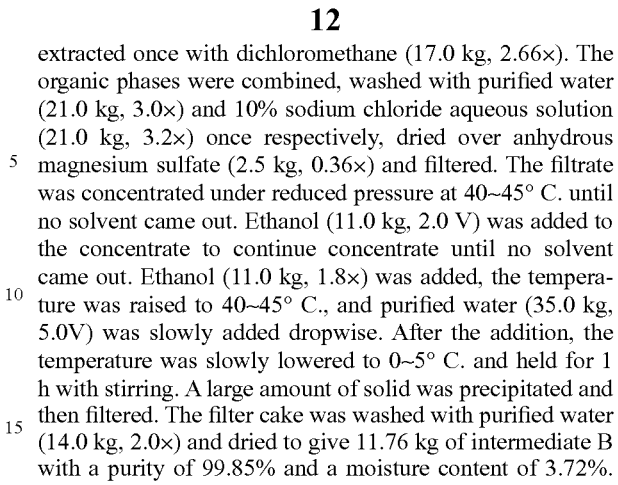

Intermediate B (5.0 kg, 1.0 eq) and tetrahydrofuran (22.5 kg, 4.5×) were added under the protection of argon, and the mixture was concentrated until no solvent came out. Tetrahydrofuran (44.5 kg, 8.9×) was added again and dissolved with stirring, and the water content was measured (KF=0.1%). The temperature of the system was lowered to −5~0° C. A tetrahydrofuran solution of isopropyl magnesium chloride (15.4 kg, 1.3 eq) was added dropwise at −5~0° C., and after the addition, the mixture was stirred at −5~0° C. for 1 hour.

Zinc chloride (3.71 kg, 1.15 eq) was added in batches while the temperature was controlled at −5~0° C. The reaction was carried out with stirring at −5~0° C. for 1.5-2 hours. Tetrakis(triphenylphosphine)palladium (0.5 kg, 0.018 eq) and SM2 (10.59 kg, 3.0 eq) were added. Then the temperature was raised to 0~5° C., and the reaction was carried out at this temperature for 2~4 hours.

5% ammonium chloride solution (15.0 kg, 3.0×) was added to quench the reaction and the temperature was controlled to lower than 25° C. The reaction system was stirred at 20~25° C. for 0.5 hour, and then concentrated at

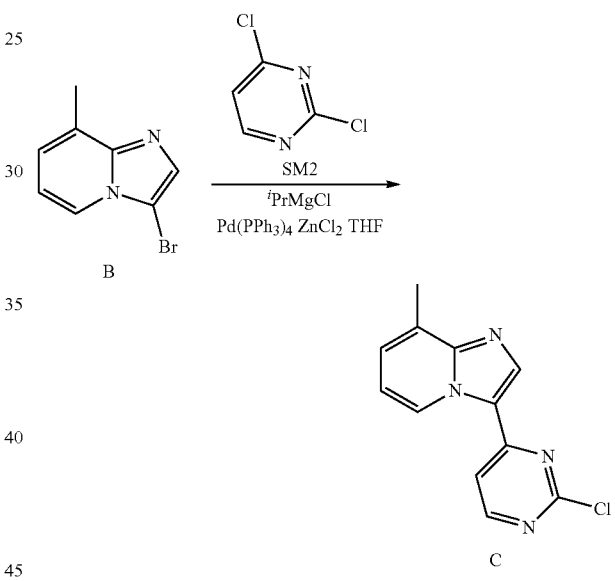

40~45° C. until no solvent came out. Purified water (25.0 kg, 5.0×) was added to continue the concentrate at 40~45° C. until almost no solvent came out. Purified water (50.0 kg, 10.0×) was added and the mixture was stirred at 20~25° C. for 2~4 hours. After centrifugation, the filter cake was rinsed with purified water (25.0 kg, 5.0×), and then suspended in purified water (75.0 kg, 15.0×) with stirring at 20~25° C. for 2~4 hours. Then the filter cake was rinsed respectively with purified water (25.0 kg, 5.0×) and purified water (25.0 kg, 5.0×), and suspended in toluene (45.0 kg, 9.0×) with stirring at 60~65° C. for 2~4 hours. The temperature was lowered to 20~25° C. After centrifugation, the filter cake was suspended in tetrahydrofuran (22.5 kg, 4.45×) with stirring at 60~65° C. for 2 hours. N-heptane (34.0 kg, 6.8×) was added and the temperature was lowered to 20~25° C. The reaction system was stirred for 2 hours. The filter cake was rinsed with tetrahydrofuran/n-heptane (1:2) and dried at 45~50° C. for 38 hours to give 5.3 kg of an off-white solid which was intermediate C with a purity of 95.26%, a content of 72.43%, and a moisture content of 9.28%. Yield: 66.2%.

LC-MS: m/z (ES+) (M+H$^+$): 245.3 (100%), $^1$HNMR (400 MHz, d$_6$-DMSO) δ 9.55 (d, J=8.0 Hz, 1H), 8.70 (s, 1H), 8.61 (d, J=8.0 Hz, 1H), 8.04 (d, J=4.0 Hz, 2H), 7.36 (d, J=8.0 Hz, 2H), 7.16 (dd apparent t, J=8.0, 8.0 Hz, 1H), 2.54 (s, 3H).

Step 4: Preparation of Intermediate D

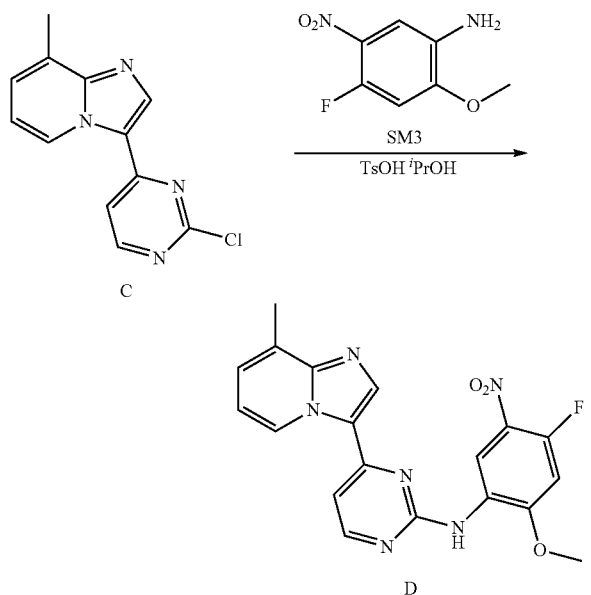

Intermediate C (3.8 kg, based on the content, 1.0 eq), XT85-SM3 (3.47 kg, 1.2 eq), p-toluenesulfonic acid monohydrate (3.84, 1.3 eq) and isopropanol (30.0 kg, 10.0 V) were added to 100 L glass reaction kettle and heated to 80-85° C. with stirring The reaction was carried out with stirring for 28-30 hours.

The temperature was slowly lowered to room temperature, and the mixture was stirring for 2 h. After filtration, the filter cake was rinsed with isopropanol (6.1 kg, 2.0×) and suspended in purified water (38.0 kg, 10.0V) with stirring at 20-25° C. for 2 h. After filtration, the filter cake was rinsed with purified water (7.6 kg, 2.0V) and resuspended with purified water (30.4 kg, 8.0V). 6% sodium bicarbonate aqueous solution (23.9 kg, 6.3×) was introduced to free the base added. After the addition, the mixture was stirred for 1 h and centrifuged. The filter cake was rinsed with purified water (7.6 kg, 2.0V) and suspended in purified water (38.0 kg, 10.0 V) with stirring at 20-25° C. for 2 h. After filtration, the filter cake was rinsed with purified water (7.6 kg, 2.0V) and suspended in isopropyl alcohol (30.0 kg, 10.0 V) with stirring at 80-85° C. for 2 h. Filtration was carried out after the temperature was lowered to room temperature. Then the filter cake was rinsed with isopropyl alcohol (6.1 kg, 2.0 V) and dried at 45-50° C. for 24 hours to give 5.88 kg of a yellow solid which was intermediate D with a content of 98.18% and a moisture content of 0.21%. Yield: 94.3%.

LC-MS m/z (ES+) (M+H$^+$): 395.2 (100%), $^1$HNMR (400 MHz, d$_6$-DMSO) δ 10.11 (s, 1H), 9.37 (s, 1H), 9.25 (s, 1H), 8.76 (d, J=8.0 Hz, 1H), 8.60 (d, J=4.0 Hz, 1H), 7.85 (d, J=4.0 Hz, 1H), 7.56 (d, J=4.0 Hz, 1H), 7.43 (dd apparent t, J=16.0 Hz, 1H), 7.31 (d, J=8.0, 8.0 Hz, 1H), 3.96 (s, 3H), 2.60 (s, 3H).

Step 5: Preparation of Intermediate E

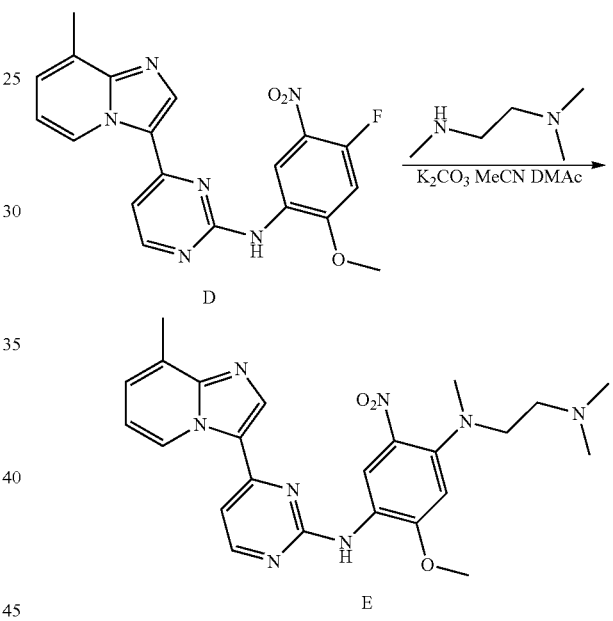

Intermediate D (1.26 kg, 3.19 mol), N,N,N'-trimethylethylenediamine (490 g, 4.79 mol) and anhydrous potassium carbonate (883 g, 6.39 mol) were added to the mixed solution of acetonitrile (10 kg) and N,N-dimethylacetamide (1.2 kg). The temperature was raised to 80-85° C., and the reaction was carried out overnight. The completion of the reaction was detected.

The temperature was slowly lowered to room temperature, and purified water (26.5 kg) was added dropwise. The mixture was stirred for 2~4 h and filtered. The filter cake was rinsed with a mixed solvent of purified water (4 kg) and acetonitrile (2 kg) and dried to give 1.4 kg of intermediate E with a purity of 97.8%. Yield: 91%.

$^1$HNMR (400 MHz, CDCl$_3$) δ 9.66 (d, J=6.9 Hz, 1H), 8.88 (s, 1H), 8.37 (d, J=5.4 Hz, 1H), 8.24 (s, 1H), 7.42 (s, 1H), 7.15 (d, J=6.9 Hz, 1H), 7.12 (d, J=5.4 Hz, 1H), 6.92 (t, J=7.0 Hz, 1H), 6.69 (s, 1H), 3.97 (s, 3H), 3.28 (t, J=6.8 Hz, 2H), 2.88 (s, 3H), 2.64 (s, 3H), 2.57 (t, J=6.8 Hz, 2H), 2.27 (s, 6H).

Step 6: Preparation of Intermediate F

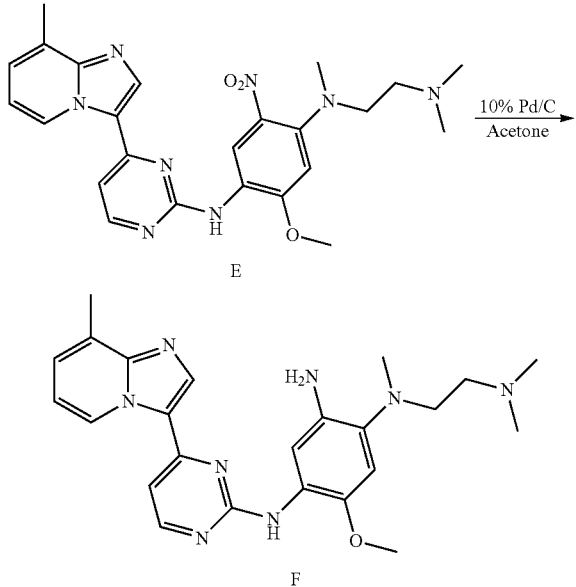

Intermediate E (600 g, 1.26 mol) and 10% wet palladium carbon (60 g) were added to acetone (9 L). Hydrogen substitution was performed three times and the pressure was maintained at 0.3 Mpa. The reaction system was heated to 40° C. and stirred for 4 h. The completion of the reaction was detected.

Methanol (9 L) was added to the reaction solution, and the mixture was stirred at 40° C. for 1~2 h. Celite was added and the mixture was filtered. The filtrate was concentrated to 1.5 L. Acetone was added to concentrate and replace the solvent 3 times (use 3.5 L acetone each time, and concentrate to 1.8 L). Methyl tert-butyl ether (4.8 L) was added dropwise to the concentrated solution and the mixture was stirred at room temperature overnight. After filtration, the wet product was rinsed with methyl tert-butyl ether (1.2 L), and the filter cake was dried to give 494 g of intermediate F with a purity of 96.6%. Yield: 88%.

$^1$HNMR (400 MHz, CDCl3) δ 9.82 (d, J=7.0 Hz, 1H), 8.34 (d, J=5.4 Hz, 1H), 8.22 (s, 1H), 7.81 (s, 1H), 7.49 (s, 1H), 7.17-7.09 (m, 1H), 7.04 (d, J=5.4 Hz, 1H), 6.91 (t, J=6.9 Hz, 1H), 6.71 (s, 1H), 3.83 (s, 3H), 2.97 (t, J=6.8 Hz, 2H), 2.68 (s, 3H), 2.64 (s, 3H), 2.42 (t, J=6.8 Hz, 2H), 2.26 (s, 6H).

Step 7: Preparation of Drug Substance H (i.e. Compound 1)

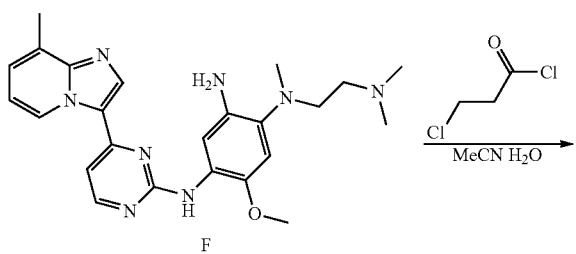

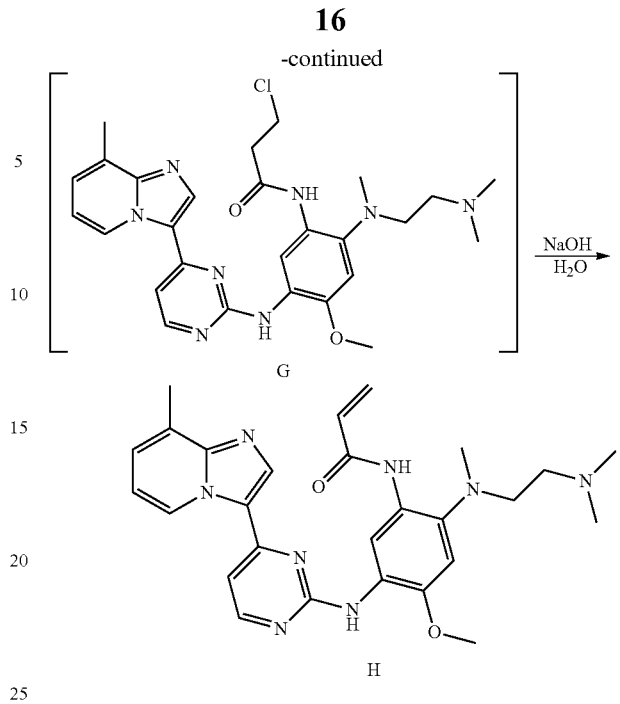

Intermediate F (1.01 kg, 2.26 mol) was added to a mixed solution of acetonitrile (4.73 kg) and water (1.52 kg), and the temperature was lowered to 0 to 5° C. 3-Chloropropionyl chloride (373 g, 2.94 mol) was added dropwise. After the addition, the mixture was stirred at 0~5° C. for 0.5 h. The completion of the reaction was detected.

An aqueous solution of sodium hydroxide (sodium hydroxide: 290 g, 7.24 mol; purified water: 505 g) was added dropwise, and the reaction was heated to 65~75° C. and stirred for 2~3 h. The completion of the reaction was detected. The reaction system was cooled to 25-35° C., and purified water (4040 g) was added dropwise. Seed crystals were added and the mixture was stirred for 1~2 h. Purified water (6060 g) was added dropwise. After the addition, the temperature was lowered to 5-10° C., and the mixture was stirred for 1~2 h and filtered. The filter cake was rinsed with a mixed solvent of acetonitrile (1.6 kg) and purified water (4 kg), and then dried to give 900 g of the drug substance H with a purity of 97.8%. Yield: 79%.

LCMS, m/z (ES+)(M+H$^+$) 501.2, $^1$HNMR (400 MHz, d$_6$-DMSO) δ 10.11 (s, 1H), 9.67 (d, J=5.8 Hz, 1H), 8.64 (s, 1H), 8.57 (s, 1H), 8.53 (s, 1H), 8.35 (d, J=5.4 Hz, 1H), 7.32 (d, J=5.4 Hz, 1H), 7.24 (d, J=6.9 Hz, 1H), 7.06 (s, 1H), 6.80 (t, J=6.9 Hz, 1H), 6.41 (dd, J=16.9, 10.1 Hz, 1H), 6.18 (dd, J=16.9, 1.9 Hz, 1H), 5.73 (dd, J=10.1, 1.9 Hz, 1H), 3.79 (s, 3H), 2.91 (t, J=5.7 Hz, 2H), 2.75 (s, 3H), 2.54 (s, 3H), 2.34 (t, J=5.8 Hz, 2H), 2.21 (s, 6H).

Characterization of the Initial Solid State of Drug Substance H (Compound 1)

Methods

1. X-Ray Powder Diffraction (XRPD)

Part of the solid sample obtained in the experiment was analyzed by a X-ray diffraction analyzer (Bruker D8 advance) equipped with a LynxEye detector. The 2θ scanning angle was from 3° to 40°, the scanning step was 0.02°, and the tube voltage and tube current were 40 KV and 40 mA, respectively. The sample was put on an XRD sample disc without background.

2. Polarized Light Microscope (PLM)

The instrument model of the polarized light microscope is Nikon Instruments Eclipse 80i. The appearance information of the sample was collected by DS camera and transferred to the computer, and then processed by NIS-Elements D3.0 software.

3. Thermogravimetric Analysis (TGA)

TA TGA Q500 was used for the thermogravimetric analysis of the solid samples. 2-3 mg of sample was placed in a balanced sample disc made of aluminum, and the sample mass was automatically weighed in a TGA heating furnace. The sample was heated at a rate of 10° C./min. During the test, the flow rate of the nitrogen to the balance and sample chambers was 40 mL/min and 60 mL/min, respectively.

4. Differential Scanning Calorimetry (DSC)

TA DSC Q200 was used for the differential scanning calorimetry of the solid samples. The standard sample used for calibration was indium. 2-3 mg sample was accurately weighed and placed in a TA DSC sample disc, and the exact mass of the sample was recorded.

The sample was heated in a nitrogen flow of 50 mL/min at a heating rate of 10° C./min.

5. $^1$H Nuclear Magnetic Analysis ($^1$H NMR)

The solid sample obtained in the salt formation screening was confirmed by $^1$H NMR. The Bruker Advance 300 equipped with B-ACS 120 autosampler system was used for $^1$H NMR analysis. Deuterated DMSO and deuterated methanol were used as solvents for NMR analysis.

6. HPLC Analysis Method 1 (Provided by PDM Analysis)

This method was provided by PDM with file number MTH-YK-001-001-RD V01. This method was used to determine the solution stability and solid stability of the drug substance H and the salt obtained by screening. The details are as follows:

Instrument: Agilent 1260
Chromatographic column: Agilent Eclipse XDB-C8, 3.5 µm, 4.6*150 mm
Column temperature: 40° C.
Mobile phase:
　A: 0.1% trifluoroacetic acid aqueous solution
　B: methanol/acetonitrile (1/1)
Gradient:

| Time (min) | Mobile phase B (%) |
|---|---|
| 0 | 20 |
| 5 | 20 |
| 30 | 40 |
| 35 | 95 |
| 40 | 95 |

Flow rate: 1.0 mL/min
Injection volume: 10 µL
Running time: 40 min

Figure 2:
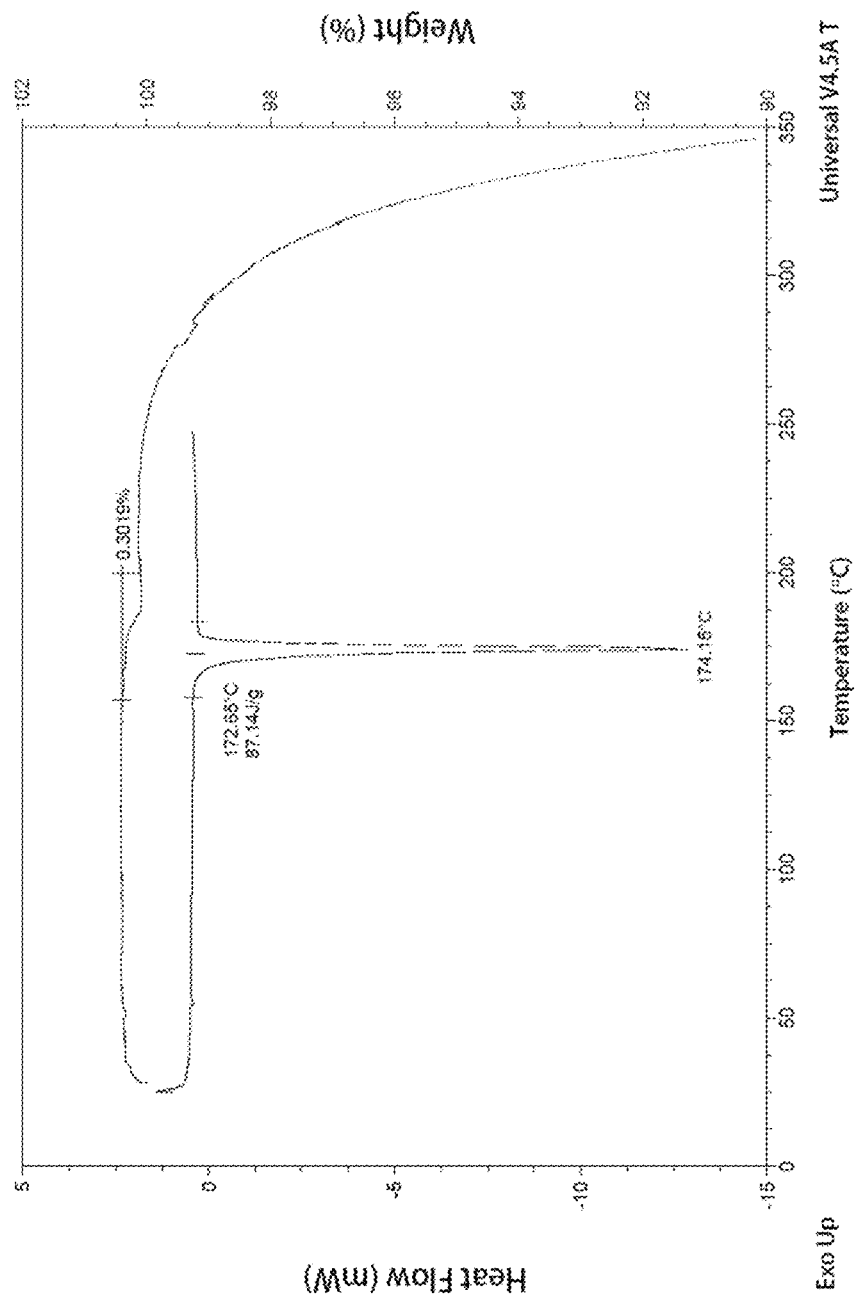
FIG. 2: TGA and DSC spectra of the crystal form A of Compound 1.
Figure 11:
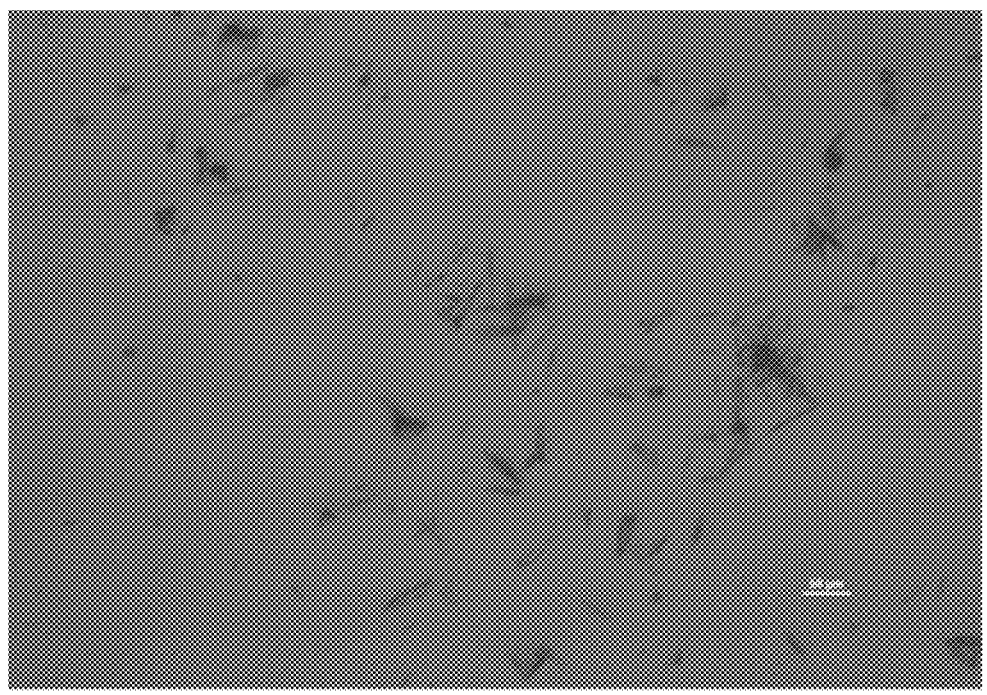
FIG. 11: polarized light microscope (PLM) image of the crystal form A of Compound 1.

The drug substance H (Compound 1) is a crystalline compound, i.e. the crystal form A of Compound 1, which was characterized by PLM, XRPD, TGA, DSC and DVS. PLM and XRPD (FIG. 11 and FIG. 2) confirmed that the drug substance H (Compound 1) has a needle-like crystal structure. FIG. 2 shows that the drug substance sample has a weight loss of 0.3% at about 180° C. There is an endothermic peak in the DSC spectrum, which should be the melting peak of the sample. The starting temperature of this peak is 172.65° C.

Figure 3:
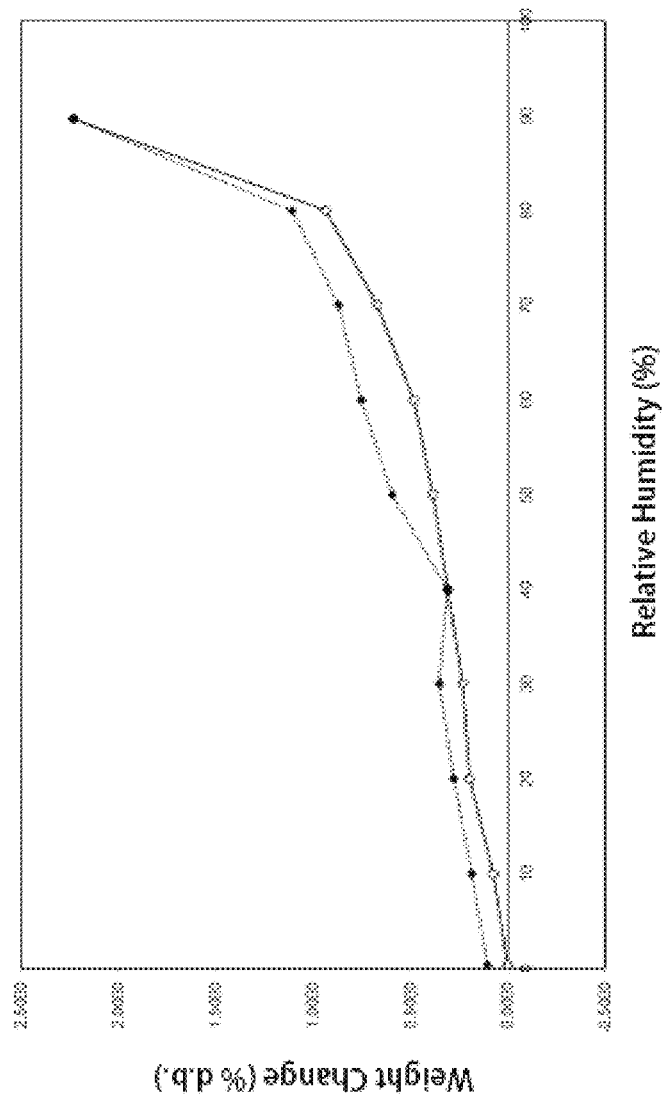
FIG. 3: DVS graph of the crystal form A of Compound 1.
Figure 4:
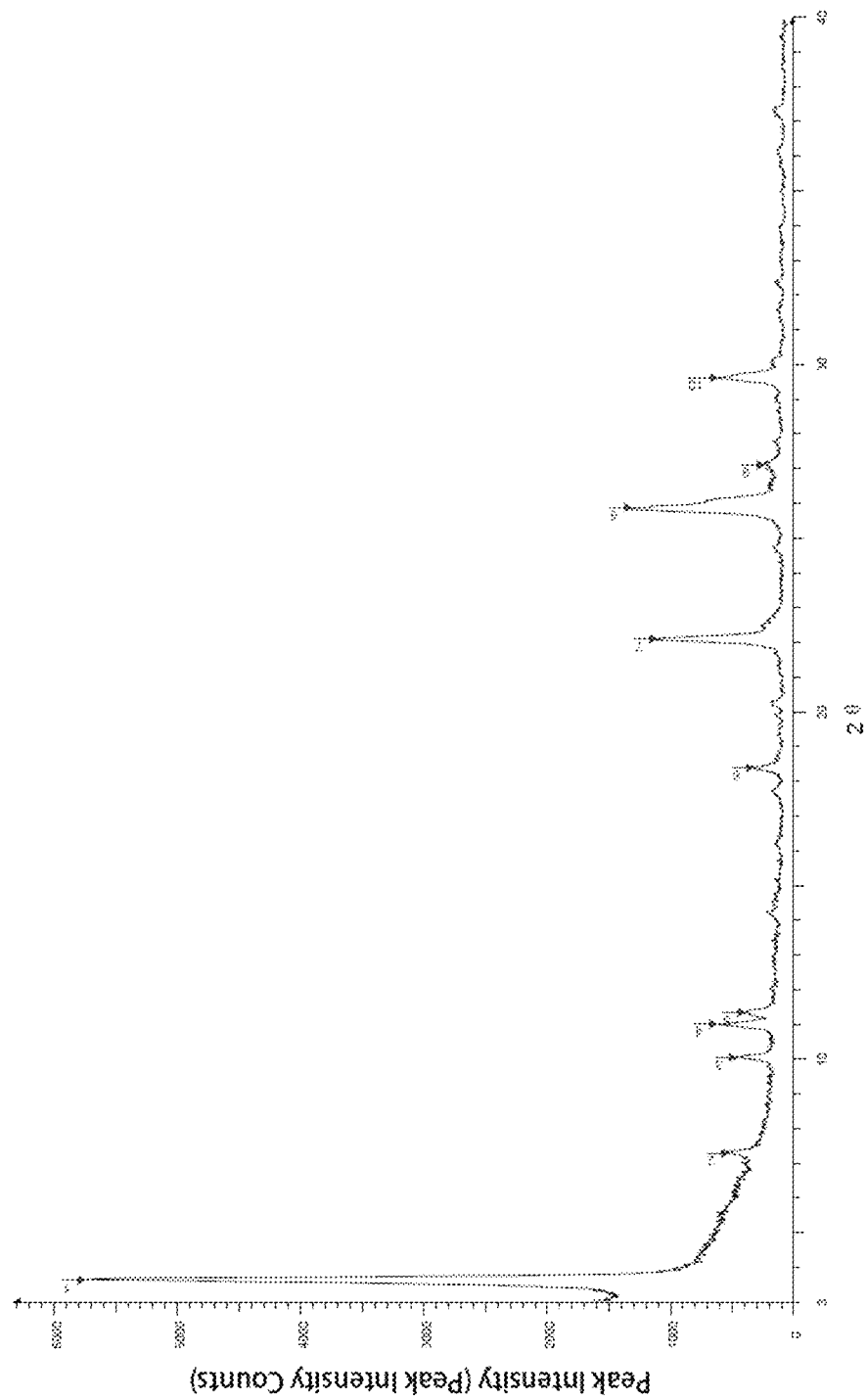
FIG. 4: XRPD pattern of the crystal form I of the hydrochloride of Compound 1.
Figure 5:
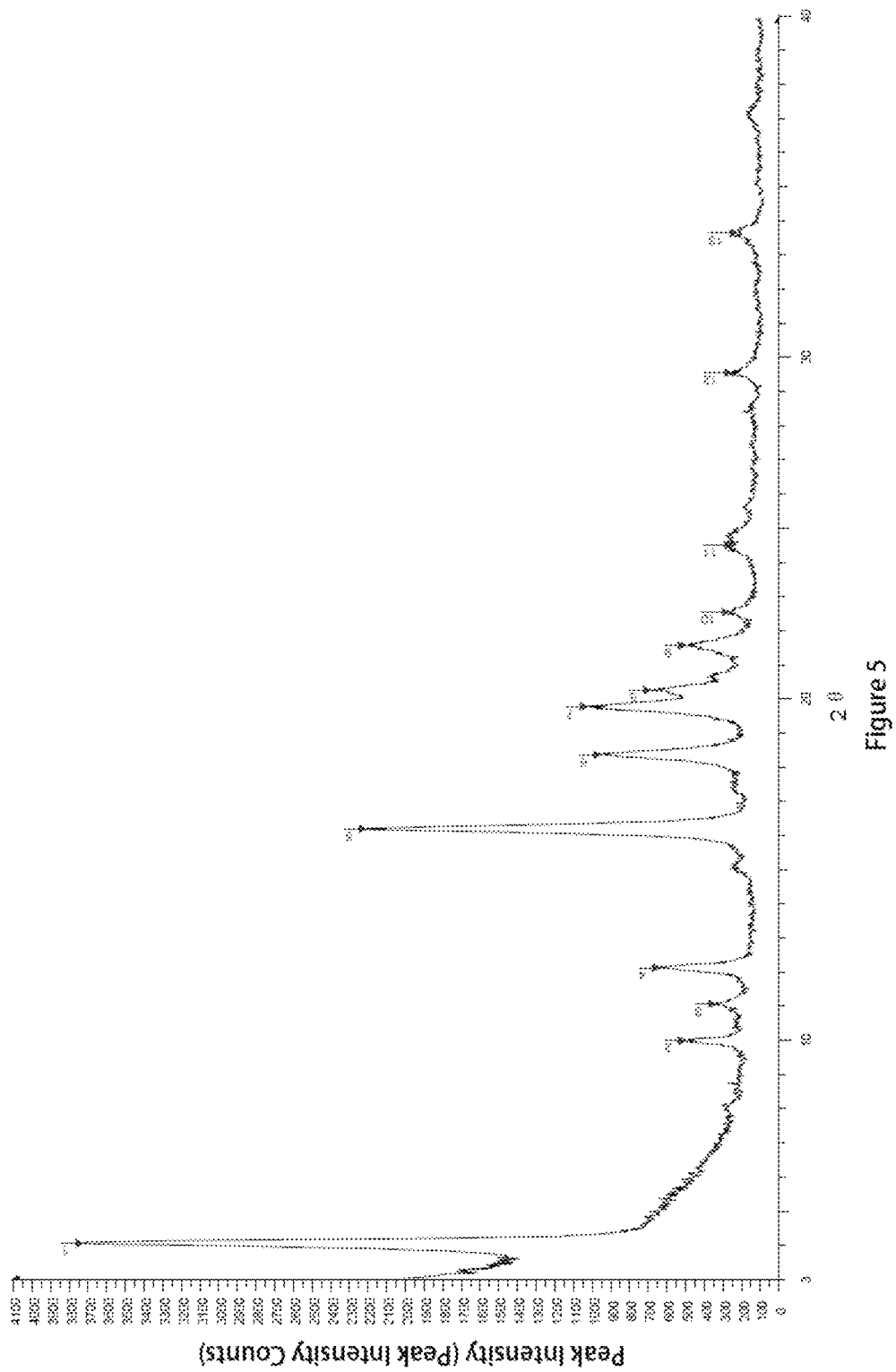
FIG. 5: XRPD pattern of the crystal form II of the mesylate of Compound 1.
Figure 6:
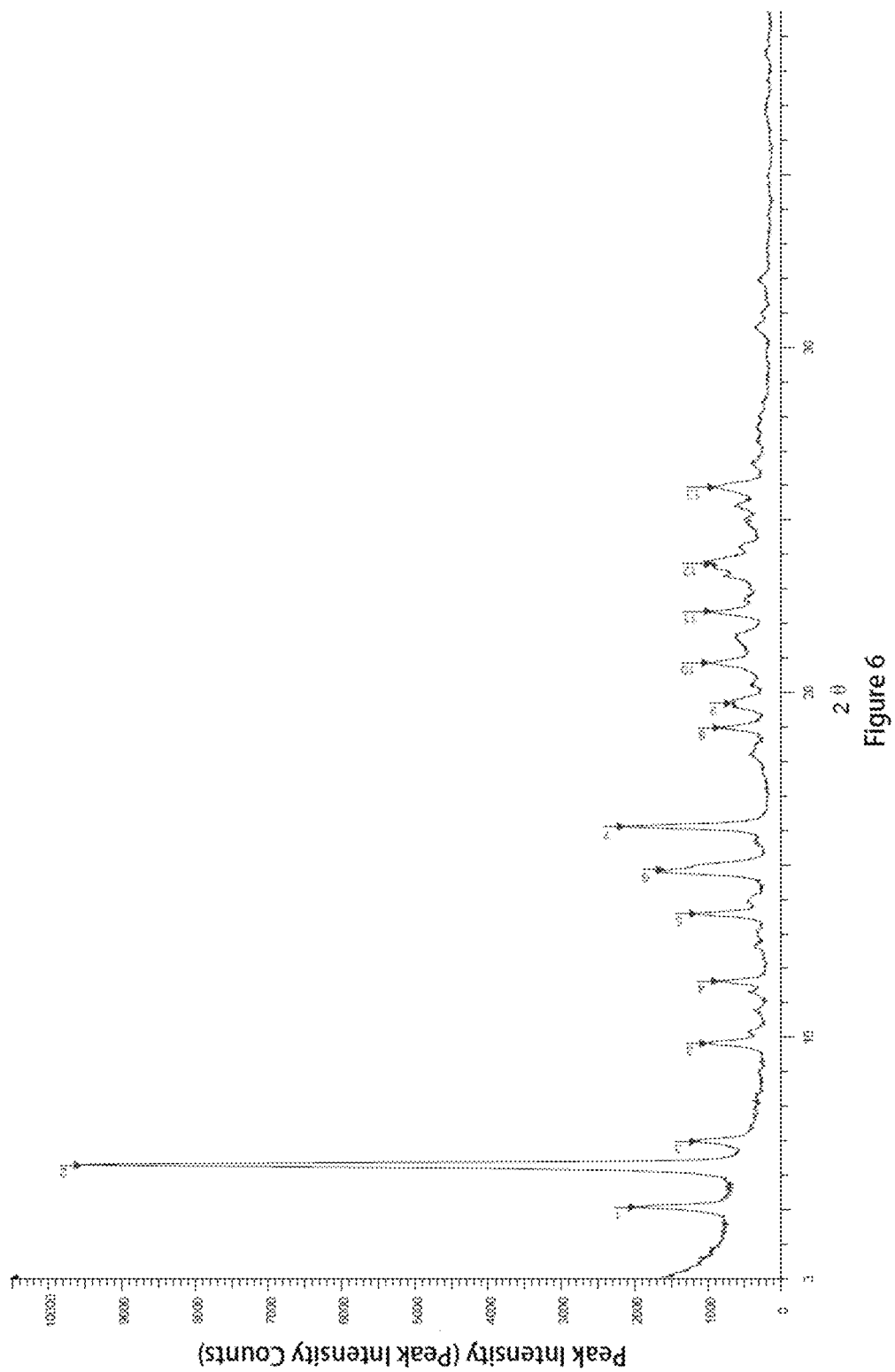
FIG. 6: XRPD pattern of the crystal form III of the fumarate of Compound 1.
Figure 7:
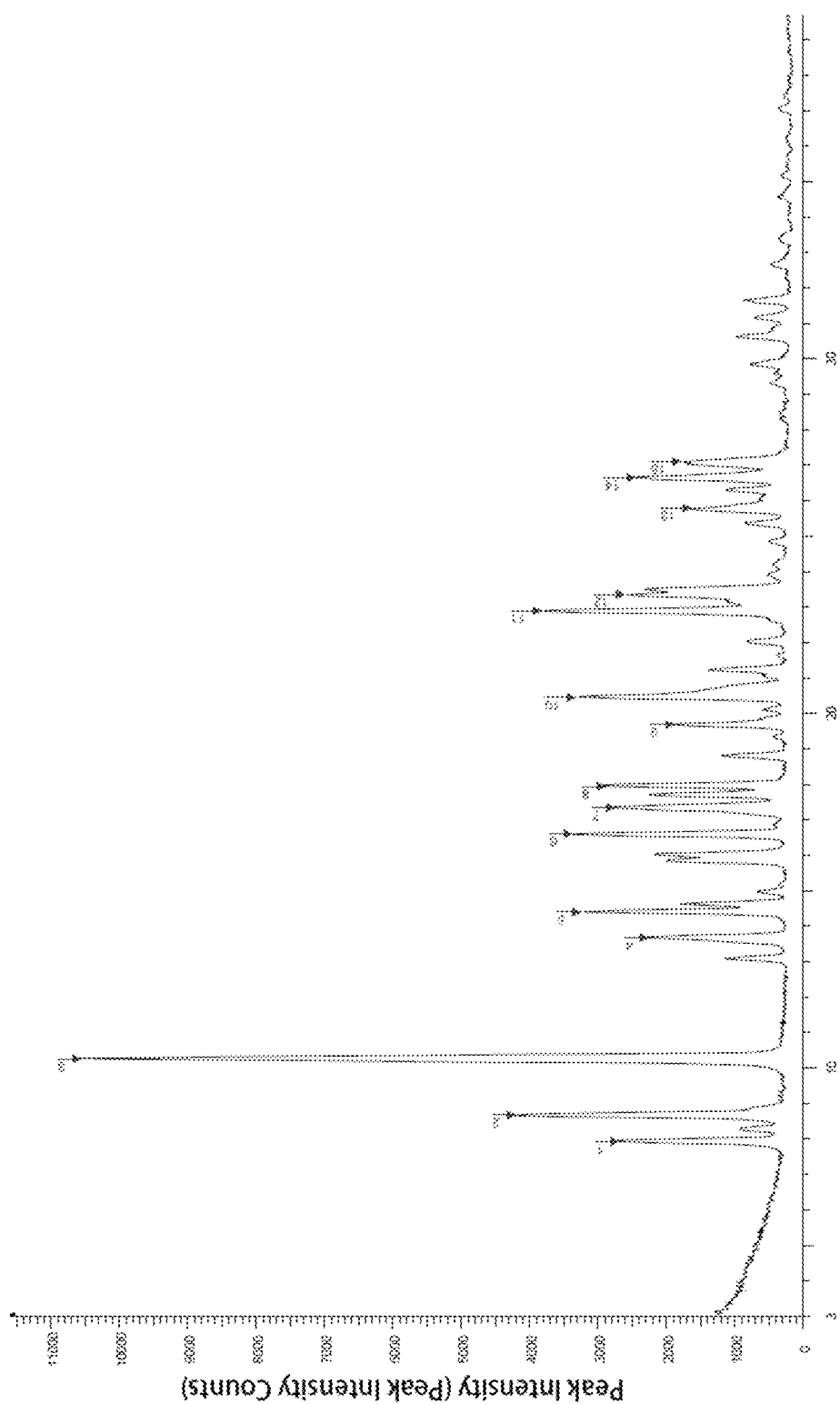
FIG. 7: XRPD pattern of the crystal form IV of the benzoate of Compound 1.
Figure 8:
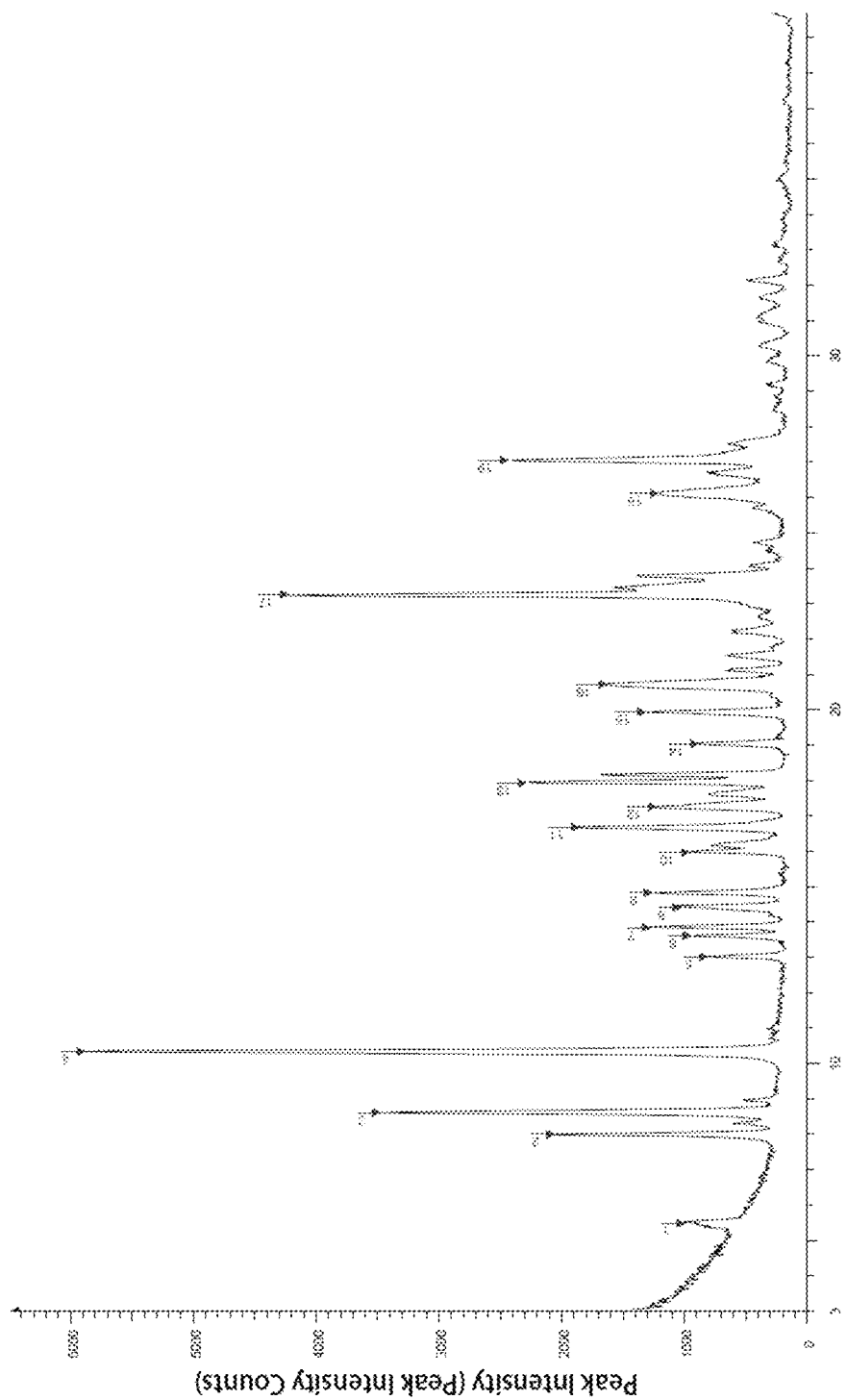
FIG. 8: XRPD pattern of the crystal form V of the maleate of Compound 1.
Figure 9:
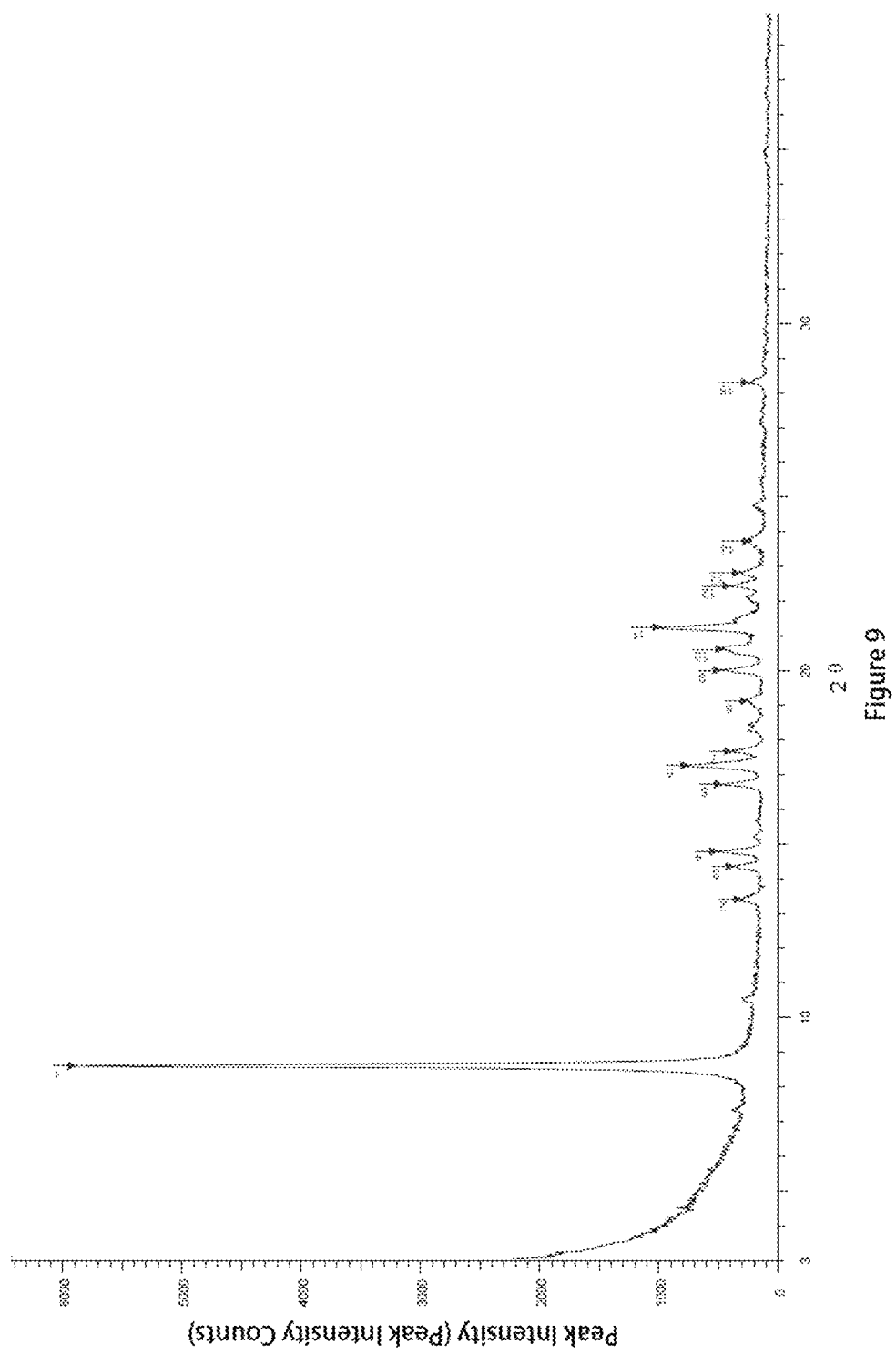
FIG. 9: XRPD pattern of the crystal form VI of the L-tartrate of Compound 1.
Figure 10:
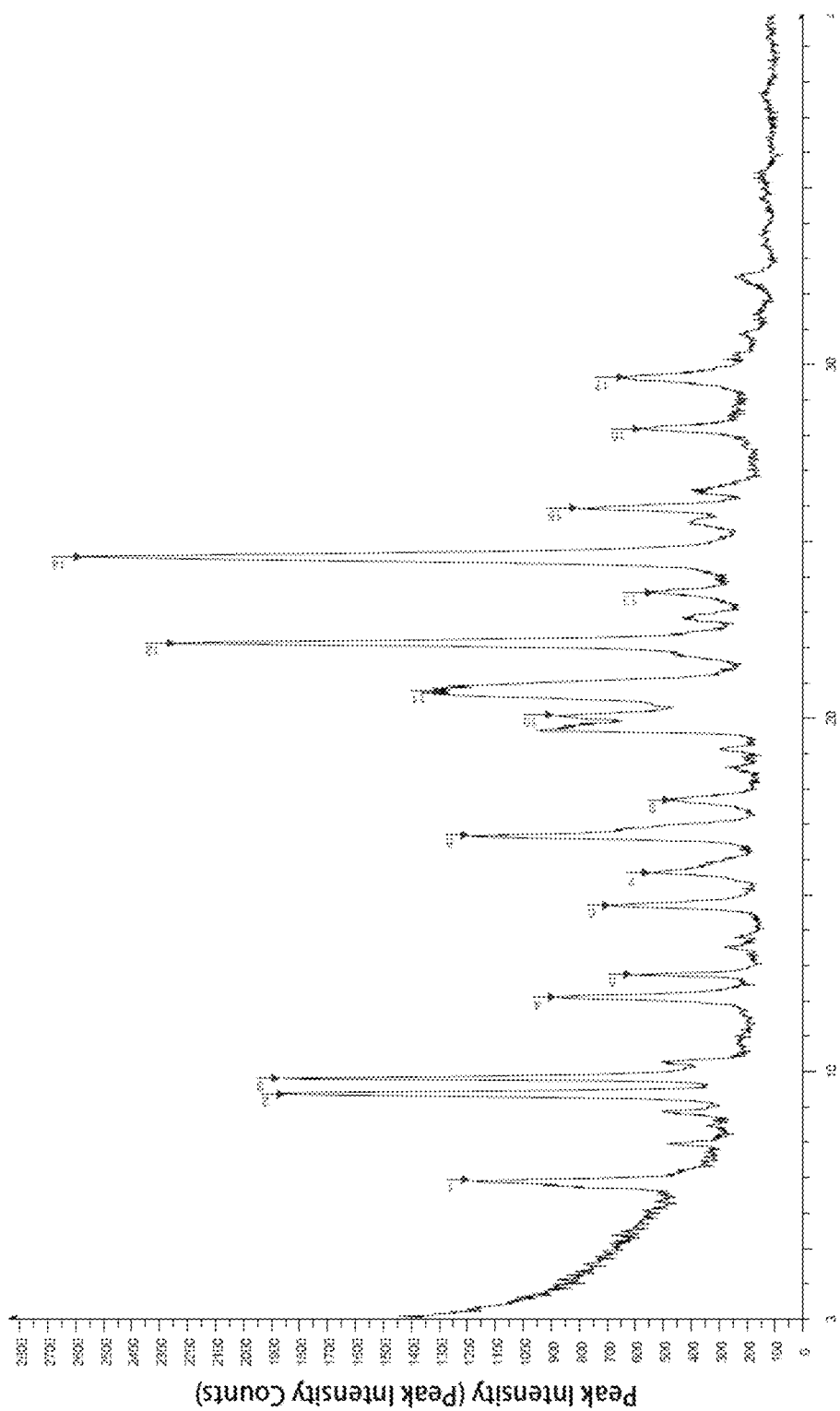
FIG. 10: XRPD pattern of the crystal form VII of the succinate of Compound 1.

The DVS measurement results (FIG. 3) show that the moisture absorption of the sample was 0.934% at 80% RH. After DVS measurement, the sample was analyzed by XRPD again. The result shows that the crystal structure of the sample did not change (FIG. 2).

II. Method of Producing Crystal Forms of the Pharmaceutically Acceptable Salt of Compound 1

Example 1: Method of Producing Crystal Form IV of Benzoate of Compound 1

Compound 1 (700 g, 1.39 mol) was added to a mixed solution of methanol (700 ml) and acetone (8.4 L), heated to 60° C., and stirred until dissolved thoroughly. A solution of benzoic acid (170.7 g, 1.39 mol) in acetone (1.4 L) was added dropwise, and the mixture was stirred at 60° C. for 1 h. Then the temperature was lowered to 20~25° C. and the mixture was stirred for 2 h. After filtration, the filter cake was rinsed with acetone (3.4 L) and then dried to give 770 g of the benzoate of Compound 1 with a purity of 99.0%. Yield: 88%.

m/z (ES+)(M+H$^±$)=501.2, $^1$H NMR (400 MHz, DMSO) δ=10.07 (s, 1H), 9.68 (s, 1H), 8.65 (s, 1H), 8.55 (d, J=11.6 Hz, 2H), 8.35 (d, J=5.1 Hz, 1H), 7.96 (d, J=7.0 Hz, 2H), 7.58 (d, J=7.2 Hz, 1H), 7.48 (t, J=7.3 Hz, 2H), 7.33 (d, J=5.2 Hz, 1H), 7.23 (d, J=6.3 Hz, 1H), 7.06 (s, 1H), 6.82 (s, 1H), 6.48 (dd, J=16.7, 10.2 Hz, 1H), 6.18 (d, J=16.8 Hz, 1H), 5.71 (d, J=10.1 Hz, 1H), 3.80 (s, 3H), 2.97 (t, J=6.9 Hz, 2H), 2.74 (s, 3H), 2.58-2.43 (m, 5H), 2.30 (s, 6H).

The crystal form IV is the crystal form of the benzoate of Compound 1.

Figure 12:
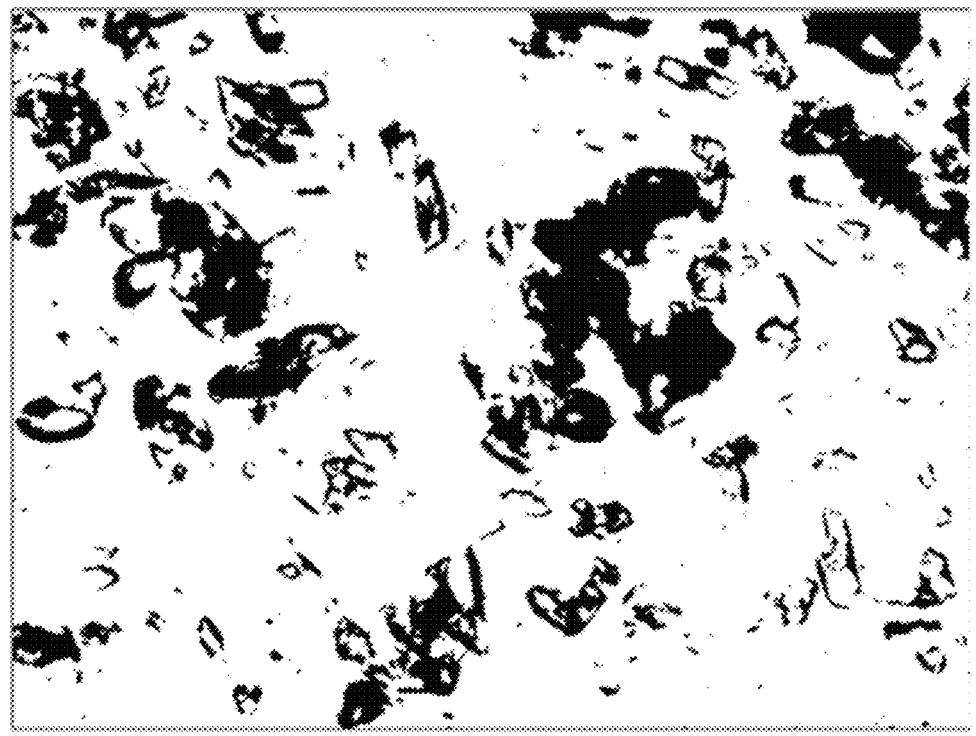
FIG. 12: polarized light microscope (PLM) image of the crystal form IV of the benzoate of Compound 1.

The PLM image of the crystal form IV of the benzoate of Compound 1 is shown in FIG. 12.

The crystal form IV of the benzoate of Compound 1 has diffraction peaks in X-ray powder diffraction at diffraction angles (2θ±0.2°): 7.863, 8.601, 10.197, 13.055, 13.591, 14.376, 16.53, 17.314, 17.944 and 22.892.

| Number | Angle 2-θ° | d Angstrom | Intensity Counts | Relative Intensity % | Net Area Cps × 2-θ° | Relative Area (%) | Width at Half Maximum 2-θ° |
|---|---|---|---|---|---|---|---|
| 1 | 7.863 | 11.23494 | 696 | 32.4 | 2.934 | 20.85 | 0.119 |
| 2 | 8.601 | 10.2726 | 2072 | 96.3 | 7.783 | 55.32 | 0.085 |
| 3 | 10.197 | 8.66812 | 2151 | 100 | 14.07 | 100.00 | 0.167 |
| 4 | 13.055 | 6.77624 | 481 | 22.4 | 1.906 | 13.55 | 0.113 |
| 5 | 13.591 | 6.50979 | 297 | 13.8 | 1.767 | 12.56 | 0.194 |
| 6 | 14.376 | 6.15628 | 752 | 35 | 4.125 | 29.32 | 0.12 |
| 7 | 16.53 | 5.35841 | 1205 | 56 | 4.937 | 35.09 | 0.11 |
| 8 | 17.314 | 5.1176 | 649 | 30.2 | 2.979 | 21.17 | 0.122 |
| 9 | 17.944 | 4.93921 | 304 | 14.1 | 0.947 | 6.73 | 0.116 |
| 10 | 22.892 | 3.88163 | 826 | 38.4 | 3.278 | 23.30 | 0.119 |

Figure 13:
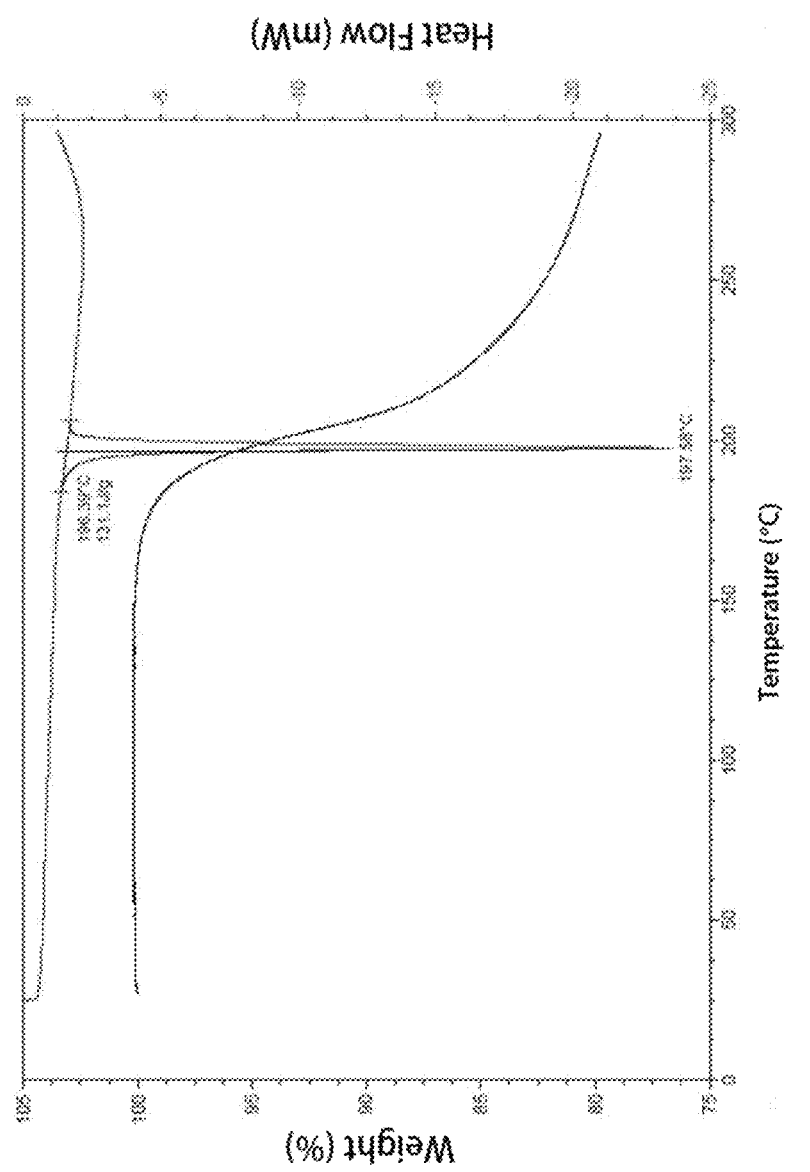
FIG. 13: TGA and DSC spectra of the crystal form IV of the benzoate of Compound 1.

The TGA and DSC spectra of the crystal form IV of the benzoate of Compound 1 are shown in FIG. 13.

Generally speaking, error range of the diffraction angle (2θ) in X-ray powder diffraction is within ±0.2°. Therefore, it should be understood that the above value of the diffraction angle also comprises a value within a range of about ±0.2°. Therefore, the present disclosure comprises not only crystals having same diffraction angles and peaks in X-ray powder diffraction, but also crystals having diffraction angles agree with the indicated values with an error of ±0.2°.

Example 2: Method of Producing Crystal Form I of Hydrochloride of Compound 1

25.28 mg of the drug substance H (Compound 1) was added to 1 mL of acetonitrile, and the mixture was stirred at 60° C. until dissolved thoroughly. After the addition of 150 μL of 1 M hydrochloric acid in methanol solution, a brown-yellow solid was precipitated from the reaction solution. The mixture was stirred at room temperature for 30 minutes and the solid therein was filtered. The sample was dried under vacuum at room temperature overnight.

Example 3: Method of Producing Crystal Form II of Mesylate of Compound 1

25.40 mg of the drug substance H (Compound 1) was added to 1,000 μL ethyl acetate/500 μL ethanol, and the mixture was stirred at 60° C. until dissolved thoroughly. After the addition of 3.25 μL of methylsulfonic acid (1 eq.), a solid was precipitated out. The reaction was heated for 1 h and then the temperature was lowered. The mixture was stirred at room temperature overnight, and the solid therein was filtered and dried under vacuum at 40° C. for 4 h.

Example 4: Method of Producing Crystal Form III of Fumarate of Compound 1

25.27 mg of the drug substance H (Compound 1) was added to 1 mL of acetonitrile, and the mixture was stirred at 60° C. until dissolved thoroughly. After the addition of 265 μL of 0.2 M fumaric acid in methanol solution (1.05 eq.), a solid was precipitated from the reaction solution. The reaction was heated for 1 h. Then the mixture was stirred at room temperature for 30 minutes and the solid therein was filtered. The samples were dried under vacuum at room temperature overnight.

Example 5: Method of Producing Crystal Form V of Maleate of Compound 1

25.21 mg of the drug substance H was added to 1 mL of ethyl acetate, and the mixture was stirred at 60° C. until dissolved thoroughly. After the addition of 100 μL of 0.5 M maleic acid in methanol solution (1 eq.), the reaction solution was stirred at room temperature and the solution was clear. After 4 h, 500 μL of methyl tert-butyl ether was added. After stirring at room temperature for 5 min, a solid was precipitated. After continue stirring for 1 h, the solid therein was filtered and dried under vacuum at room temperature.

Example 6: Method of Producing Crystal Form VI of L-Tartrate of Compound 1

25.08 mg of the drug substance H was added to 1 mL of isopropyl alcohol, and the mixture was stirred at 60° C. until dissolved thoroughly. A yellow solid was precipitated immediately after the addition of 50 μL of 1 M tartaric acid in methanol solution (1 eq.). After the mixture was stirred at room temperature for 2.5 h, the solid therein was filtered and dried under vacuum at room temperature.

Example 7: Method of Producing Crystal Form VII of Succinate of Compound 1

25.41 mg of the drug substance H was added to 1 mL of acetonitrile, and the mixture was stirred at 60° C. until dissolved thoroughly. After the addition of 53 μL of 1 M succinic acid in methanol solution (1.05 eq.), a solid was precipitated from the reaction solution. The solution was heated and the reaction was carried out for 1 h. Then the mixture was stirred at room temperature for 30 minutes, and the solid therein was filtered and dried under vacuum at 40° C. overnight.

Properties of Crystal Forms of the Pharmaceutically Acceptable Salts of Compound 1

Solubility Assay 200 mg of the drug substance H (Compound 1), the crystal form II of the mesylate of Compound 1 (238.1 mg) and the crystal form IV of the benzoate of Compound 1 (248.8 mg) were respectively weighed and put into a 8 mL vial, each sample in duplicate. Subsequently, 2 mL of buffer solutions at pH 1.2 and 6.8 were added respectively to prepare a saturated solution. The above resulting suspensions were placed in a shaker and shaken at a speed of 200 rpm for 2 hours at 25° C. The resulting mixtures were filtered, and the filtrates were diluted by an appropriate multiple and analyzed by HPLC to determine the solubility of each sample in different media. The results showed that the solubility of the two salts in buffer solutions at pH 1.2 and 6.8 was significantly improved compared to the free base.

Results of Solubility Assay

|  | 2 h Solubility (mg/mL) | |
| --- | --- | --- |
| Sample Name | pH 1.2 | pH 6.8 |
| Compound 1 | 38.12 | 6.75 |
| Mesylate | 95.09 | 67.19 |
| Benzoate | 78.13 | 18.34 |

Bioavailability Assay

The crystalline forms of the salts formed by the reaction between Compound 1 and the acid, such as mesylate and benzoate, are powders with significantly improved solubility. This will have a beneficial effect on the in vivo absorption of the active drug. For example, benzoate has shown good absorption and bioavailability in pharmacokinetic trials of a solid dosage form administered in dogs, which has no difference in exposure and bioavailability of the active drug when compared with the administration in solution form. The details are as follows.

A single oral dose of 3 mg/kg of the benzoate of Compound 1 was given to Beagle dogs (crystalline powders encapsulated in capsules for administration). The peak time $T_{max}$ was 2 h, $T_{1/2}$ was 3.13 h, $C_{max}$ was 203.15 ng/mL, $AUC_{(0-t)}$ was 856.41 ng/mL·h, and absolute bioavailability was 51%. Absorption and elimination are similar to equivalent dose of the solution, and the relative bioavailability is 98%.

This disclosure merely illustrates some specific embodiments that are claimed, wherein the technical features described in one or more technical solutions can be combined with any one or more technical solutions, and the technical solutions obtained by combination are also within the protection scope of the present application, just as these technical solutions obtained by combination have been specifically recorded in the disclosure of the present disclosure.

The invention claimed is:

1. A crystal form A of N-(2-methoxy-4-($N^1$,$N^2$,$N^2$-trimethyl-1,2-ethylenediamine-1-yl)-5-acrylamidephenyl)-4-(8-methylimidazo[1,2-a]pyridin-3-yl)pyrimidin-2-amine, which has the following 2θ values in X-ray powder diffraction pattern: 6.625±0.2, 10.289±0.2, 13.791±0.2, 15.235±0.2, 16.019±0.2, 16.353±0.2, 17.087±0.2, 19.510±0.2, 19.992±0.2, 21.194±0.2, 21.992±0.2, 22.724±0.2, 24.338±0.2, 24.997±0.2, 25.876±0.2, and 27.245±0.2.

2. The crystal form A of N-(2-methoxy-4-($N^1$,$N^2$,$N^2$-trimethyl-1,2-ethylenediamine-1-yl)-5-acrylamidephenyl)-4-(8-methylimidazo[1,2-a]pyridin-3-yl)pyrimidin-2-amine according to claim 1, which has X-ray powder diffraction pattern shown in FIG. 1.

3. A method of producing the crystal form A of N-(2-methoxy-4-($N^1$,$N^2$,$N^2$-trimethyl-1,2-ethylenediamine-1-yl)-5-acrylamidephenyl)-4-(8-methylimidazo[1,2-a]pyridin-3-yl)pyrimidin-2-amine according to claim 1, comprising the following steps:
(1) suspending N-(2-methoxy-4-($N^1$,$N^2$,$N^2$-trimethyl-1,2-ethylenediamine-1-yl)-5-acrylamidephenyl)-4-(8-methylimidazo[1,2-a]pyridin-3-yl)pyrimidin-2-amine in a mixed solvent of acetonitrile and water, heating and dissolving with stirring;
(2) cooling the solution obtained in step (1) overnight with stirring until room temperature, performing precipitation, filtration, and collecting solid; and
(3) subjecting the solid obtained in step (2) to vacuum drying to obtain the crystal form A of N-(2-methoxy-4-($N^1$,$N^2$,$N^2$-trimethyl-1,2-ethylenediamine-1-yl)-5-acrylamidephenyl)-4-(8-methylimidazo[1,2-a]pyridin-3-yl)pyrimidin-2-amine.

4. A crystal form II of N-(2-methoxy-4-($N^1$,$N^2$,$N^2$-trimethyl-1,2-ethylenediamine-1-yl)-5-acrylamidephenyl)-4-(8-methylimidazo[1,2-a]pyridin-3-yl)pyrimidin-2-amine mesylate, which has the following 2θ values in X-ray powder diffraction pattern: 4.015±0.2, 9.963±0.2, 11.032±0.2, 12.099±0.2, 16.179±0.2, 18.353±0.2, 19.762±0.2, 20.250±0.2, 21.565±0.2, 22.541±0.2, 24.507±0.2, 29.554±0.2, and 33.666±0.2.

5. A crystal form IV of N-(2-methoxy-4-($N^1$,$N^2$,$N^2$-trimethyl-1,2-ethylenediamine-1-yl)-5-acrylamidephenyl)-4-(8-methylimidazo[1,2-a]pyridin-3-yl)pyrimidin-2-amine benzoate, which has the following 2θ values in X-ray powder diffraction pattern: 7.994±0.2, 8.696±0.2, 10.307±0.2, 14.471±0.2, 16.639±0.2, 17.377±0.2, 17.967±0.2, 19.723±0.2, 20.529±0.2, 22.933±0.2, and 23.383±0.2.

6. A method of producing the crystal form A of N-(2-methoxy-4-($N^1$,$N^2$,$N^2$-trimethyl-1,2-ethylenediamine-1-yl)-5-acrylamidephenyl)-4-(8-methylimidazo[1,2-a]pyridin-3-yl)pyrimidin-2-amine according to claim 2, comprising the following steps:
(1) suspending N-(2-methoxy-4-($N^1$,$N^2$,$N^2$-trimethyl-1,2-ethylenediamine-1-yl)-5-acrylamidephenyl)-4-(8-methylimidazo[1,2-a]pyridin-3-yl)pyrimidin-2-amine in a mixed solvent of acetonitrile and water, heating and dissolving with stirring;
(2) cooling the solution obtained in step (1) overnight with stirring until room temperature, performing precipitation, filtration, and collecting solid; and
(3) subjecting the solid obtained in step (2) to vacuum drying to obtain the crystal form A of N-(2-methoxy-4-($N^1$,$N^2$,$N^2$-trimethyl-1,2-ethylenediamine-1-yl)-5-acrylamidephenyl)-4-(8-methylimidazo[1,2-a]pyridin-3-yl)pyrimidin-2-amine.

* * * * *

UNITED STATES PATENT AND TRADEMARK OFFICE
CERTIFICATE OF CORRECTION

PATENT NO. : 10,906,901 B2
APPLICATION NO. : 16/631276
DATED : February 2, 2021
INVENTOR(S) : Maosheng Duan It is certified that error appears in the above-identified patent and that said Letters Patent is hereby corrected as shown below:

On the Title Page

Item (71) Applicant, delete "HAINAN YUEKANG BIOMEDICINES CO., LTD., Hainan, (CN)" and replace with --HAINAN YUEKANG BIOMEDICINES CO., LTD., Haikou, Hainan, (CN)-- therefor.

Item (72) Inventor, delete "Maosheng DUAN, Hainan, (CN)" and replace with --Maosheng DUAN, Haikou, Hainan, (CN)-- therefor.

Signed and Sealed this
Sixth Day of April, 2021

Drew Hirshfeld
*Performing the Functions and Duties of the
Under Secretary of Commerce for Intellectual Property and
Director of the United States Patent and Trademark Office*